(12) United States Patent
Shigeta

(10) Patent No.: US 10,004,389 B2
(45) Date of Patent: Jun. 26, 2018

(54) ENDOSCOPE SYSTEM, OPERATION METHOD FOR ENDOSCOPE SYSTEM, PROCESSOR DEVICE, AND OPERATION METHOD FOR PROCESSOR DEVICE

(71) Applicant: FUJIFILM Corporation, Tokyo (JP)

(72) Inventor: Norimasa Shigeta, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 322 days.

(21) Appl. No.: 14/665,760

(22) Filed: Mar. 23, 2015

(65) Prior Publication Data
US 2015/0272429 A1    Oct. 1, 2015

(30) Foreign Application Priority Data

Mar. 31, 2014  (JP) ................................ 2014-074279

(51) Int. Cl.
| | | |
|---|---|---|
| *A61B 1/045* | (2006.01) | |
| *H04N 5/232* | (2006.01) | |
| *A61B 1/00* | (2006.01) | |
| *G06F 19/00* | (2018.01) | |
| *A61B 1/06* | (2006.01) | |

(52) U.S. Cl.
CPC ............ *A61B 1/045* (2013.01); *A61B 1/0002* (2013.01); *A61B 1/0005* (2013.01); *A61B 1/00009* (2013.01); *A61B 1/00188* (2013.01); *A61B 1/0653* (2013.01); *G06F 19/321* (2013.01); *H04N 5/23212* (2013.01);
(Continued)

(58) Field of Classification Search
USPC ......................................................... 348/65
See application file for complete search history.

(56) References Cited

U.S. PATENT DOCUMENTS

2007/0223797 A1 * 9/2007 Kaneko .............. A61B 1/00009
                                                      382/128
2012/0071718 A1 * 3/2012 On ....................... A61B 1/0661
                                                      600/109
(Continued)

FOREIGN PATENT DOCUMENTS

| EP | 1 844 697 A1 | 10/2007 |
|---|---|---|
| EP | 2 638 843 A1 | 9/2013 |

(Continued)

OTHER PUBLICATIONS

Machine translation of JP 2005-044004A.*
(Continued)

*Primary Examiner* — Behrooz Senfi
*Assistant Examiner* — Ana Picon-Feliciano
(74) *Attorney, Agent, or Firm* — Birch, Stewart, Kolasch & Birch, LLP

(57) ABSTRACT

The endoscope system includes an image signal acquisition processing unit and an image generation unit that acquire a first still image and a video or a second still image before and after acquisition of the first still image based on an image signal obtained by imaging an observation target using an image sensor, an association unit that associates the first still image with the video or associates the first still image with the second still image, and a storage unit that stores the first still image and the video associated with each other or stores the first still image and the second still image associated with each other.

20 Claims, 22 Drawing Sheets

(52) U.S. Cl.
CPC ..... *H04N 5/23245* (2013.01); *H04N 5/23296* (2013.01); *A61B 1/0638* (2013.01)

(56) References Cited

U.S. PATENT DOCUMENTS

| | | | | |
|---|---|---|---|---|
| 2014/0049628 A1* | 2/2014 | Motomura | ........... | G02B 21/367 348/77 |
| 2014/0111628 A1 | 4/2014 | Yoshino et al. | | |
| 2014/0210972 A1* | 7/2014 | On | ........... | G02B 7/36 348/65 |

FOREIGN PATENT DOCUMENTS

| | | | | |
|---|---|---|---|---|
| EP | 2 647 331 A1 | | 10/2013 | |
| JP | 2005-44004 A | | 2/2005 | |
| JP | 2005044004 A | * | 2/2005 | |
| JP | 2010-124921 A | | 6/2010 | |
| JP | 2013-230319 A | | 11/2013 | |
| JP | 2013230319 A | * | 11/2013 | |
| JP | 2013-240522 A | | 12/2013 | |
| JP | 2013240522 A | * | 12/2013 | |
| WO | WO 2013/027460 A1 | | 2/2013 | |

OTHER PUBLICATIONS

Machine translation of JP 2013-240522 A1.*
Machine translation of JP 2013-230319 A.*
Tsunakawa et al. (Machine translation of JP 2005-044004A).*
Extended European Search Report, dated Aug. 11, 2015, for European Application No. 15159140.1.
Notice of Reasons for Rejection issued in corresponding JP Application No. 2014-074279 dated May 11, 2016 with English machine translation.
European Office Communication, dated Apr. 3, 2017, for European Application No. 15 159 140.1.
European Office Communication, dated Oct. 6, 2017, for corresponding European Application No. 15159140.1.

* cited by examiner

ENDOSCOPE SYSTEM, OPERATION METHOD FOR ENDOSCOPE SYSTEM, PROCESSOR DEVICE, AND OPERATION METHOD FOR PROCESSOR DEVICE

CROSS-REFERENCE TO RELATED APPLICATIONS

The present application claims priority under 35 U.S.C. § 119 to Japanese Patent Application No. 2014-074279, filed Mar. 31, 2014, all of which are hereby expressly incorporated by reference into the present application.

BACKGROUND OF THE INVENTION

1. Field of the Invention

The present invention relates to an endoscope system for imaging an observation target in a subject, an operation method for an endoscope system, a processor device, and an operation method for a processor device.

2. Description of the Related Art

In the medical field, it is common to perform diagnosis by observing an image obtained by imaging an observation target (mucous membrane of the digestive tract or the like) in a subject using an endoscope system. The endoscope system includes a light source device that generates illumination light for irradiating an observation target, an endoscope that has an insertion unit inserted into the subject and images the observation target with an image sensor provided at the distal end of the insertion unit, and a processor device that generates an image of the observation target based on an image signal output from the image sensor and displays the image on a monitor. The endoscope system sequentially displays images of the observation target in real time on the monitor. That is, in the endoscope system, a video of the observation target is displayed on the monitor. A doctor performs diagnosis while observing the video displayed on the monitor.

In addition, the endoscope system includes a freeze button for inputting an instruction to acquire a still image of the observation target. When the freeze button is pressed, the endoscope system acquires a still image of the observation target and stores the still image as a record of observation or the like in a storage unit (for example, a non-volatile memory) provided in the processor device, for example. In addition, an endoscope system including an imaging optical system allowing a zoom operation is known. In recent years, an endoscope system is known that, when acquiring a still image in response to the pressing of the freeze button, a part of the acquired still image is enlarged based on the imaging magnification determined by the zoom operation and is displayed on the monitor together with a video of the observation target so that diagnosis can be easily performed in real time (refer to JP2013-240522A).

SUMMARY OF THE INVENTION

The still image acquired in response to the pressing of the freeze button is used for creation of a medical record that is a record of diagnosis, recording of cases, verification of diagnostic content, re-diagnosis, and the like (hereinafter, referred to as re-diagnosis and the like) after real-time diagnosis performed based on the video of the observation target displayed on the monitor. For the re-diagnosis and the like, only the still image obtained by the acquisition instruction can be generally used. Therefore, there are few diagnostic materials compared with real-time diagnosis in which diagnosis can be performed while changing the observation conditions arbitrarily. For this reason, when the endoscope system acquires a still image used for re-diagnosis and the like, it is preferable to automatically acquire a second still image or a video associated with the still image in order to support the re-diagnosis and the like.

It is an object of the invention to provide an endoscope system, an operation method for an endoscope system, a processor device, and an operation method for a processor device that support re-diagnosis and the like by automatically acquiring a second still image or a video associated with a first still image used for the re-diagnosis and the like in addition to the first still image.

An endoscope system of the invention includes: an acquisition unit that acquires a first still image and a video or a second still image before and after acquisition of the first still image based on an image signal obtained by imaging an observation target using an image sensor; an association unit that associates the first still image with the video or associates the first still image with the second still image; and a storage unit that stores the first still image and the video associated with each other or stores the first still image and the second still image associated with each other.

It is preferable to further include a first still image acquisition operation unit for inputting a first still image acquisition instruction to acquire the first still image and a control unit that performs control to acquire the first still image based on the first still image acquisition instruction and to automatically acquire the video.

Preferably, a first mode and a second mode different from the first mode are prepared as modes for acquiring the first still image and the video or the second still image, and the control unit performs control to acquire the first still image in one of the first and second modes based on the first still image acquisition instruction and then acquire the video by switching the one mode to the other mode.

It is preferable to further include an imaging optical system capable of changing an imaging magnification of the observation target, an imaging magnification change operation unit for inputting an imaging magnification change instruction to change the imaging magnification to the imaging optical system, and a control unit that performs control to acquire the first still image based on the imaging magnification change instruction and to acquire the second still image after acquisition of the first still image.

Preferably, a first mode and a second mode different from the first mode are prepared as modes for acquiring the first still image and the video or the second still image, and the control unit performs control to acquire the first still image in one of the first and second modes and then acquire the second still image by switching the one mode to the other mode.

It is preferable to further include a focus detection unit that detects a focus of an image to be acquired. Preferably, the control unit performs control to acquire the first still image when an operation of increasing the imaging magnification using the imaging magnification change operation unit is detected and to acquire the second still image when the focus detection unit detects that the image is in focus after acquisition of the first still image.

Preferably, the control unit performs control to acquire the first still image when an operation of reducing the imaging magnification using the imaging magnification change operation unit is detected and to acquire the second still image when an operation end of the imaging magnification change operation unit is detected after acquisition of the first still image.

It is preferable to further include an imaging optical system capable of changing an imaging magnification of the observation target; an imaging magnification change operation unit for inputting an imaging magnification change instruction to change the imaging magnification to the imaging optical system; and a control unit that performs control to acquire the first still image and start acquisition of the video based on the imaging magnification change instruction and to end the acquisition of the video when an operation end of the imaging magnification change operation unit is detected.

Preferably, a first mode and a second mode different from the first mode are prepared as modes for acquiring the first still image and the video or the second still image, and the control unit performs control to acquire the first still image in one of the first and second modes and then start acquisition of the video by switching the one mode to the other mode.

It is preferable to further include a display control unit that displays a plurality of the first still images stored in the storage unit side by side on a monitor and a selection unit for selecting the plurality of first still images displayed side by side on the monitor. Preferably, when the video associated with the first still images is stored in the storage unit, the display control unit displays the first still image selected by the selection unit on the monitor in an enlarged manner and reproduces the video, which is associated with the selected first still image, on the monitor.

It is preferable to further include a display control unit that displays a plurality of the first still images stored in the storage unit side by side on a monitor and a selection unit for selecting the plurality of first still images displayed side by side on the monitor. Preferably, when the second still image associated with the first still images is stored in the storage unit, the display control unit displays the first still image selected by the selection unit on the monitor in an enlarged manner and reproduces the second still image, which is associated with the selected first still image, on the monitor.

An operation method for an endoscope system includes: an acquisition step in which an acquisition unit acquires a first still image and a video or a second still image before and after acquisition of the first still image based on an image signal obtained by imaging an observation target using an image sensor; an association step in which an association unit associates the first still image with the video or associates the first still image with the second still image; and a storage step in which a storage unit stores the first still image and the video associated with each other or stores the first still image and the second still image associated with each other.

A processor device for an endoscope system of the invention includes: an acquisition unit that acquires a first still image and a video or a second still image before and after acquisition of the first still image based on an image signal obtained by imaging an observation target using an image sensor; an association unit that associates the first still image with the video or associates the first still image with the second still image; and a storage unit that stores the first still image and the video associated with each other or stores the first still image and the second still image associated with each other.

An operation method for a processor device for an endoscope system includes: an acquisition step in which an acquisition unit acquires a first still image and a video or a second still image before and after acquisition of the first still image based on an image signal obtained by imaging an observation target using an image sensor; an association step in which an association unit associates the first still image with the video or associates the first still image with the second still image; and a storage step in which a storage unit stores the first still image and the video associated with each other or stores the first still image and the second still image associated with each other.

According to the endoscope system, the operation method for an endoscope system, the processor device, and the operation method for a processor device of the invention, it is possible to support re-diagnosis and the like by automatically acquiring a second still image or a video associated with a first still image used for re-diagnosis and the like in addition to the first still image and storing the first still image and the second still image or the video so as to be associated with each other.

BRIEF DESCRIPTION OF THE DRAWINGS

FIG. 9 is a flowchart showing the operation when displaying a first still image for re-diagnosis and the like.

DESCRIPTION OF THE PREFERRED EMBODIMENTS

First Embodiment

Figure 1:
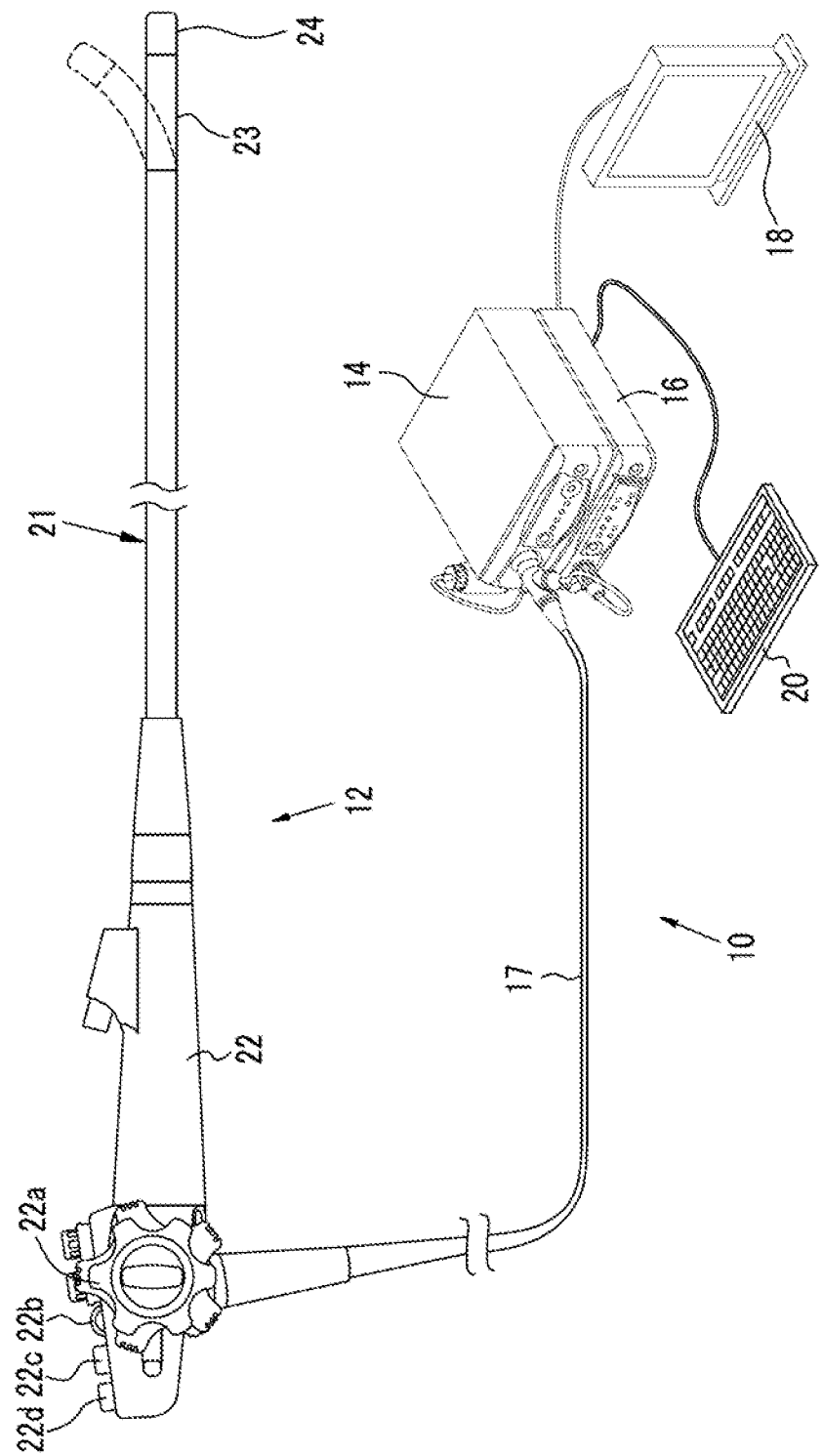
FIG. 1 is an external view of an endoscope system.

As shown in FIG. 1, an endoscope system 10 includes an endoscope 12, a light source device 14, a processor device 16, a monitor 18, and a console 20. The endoscope 12 is optically connected to the light source device 14, and is electrically connected to the processor device 16. The endoscope 12 includes an insertion unit 21 that is inserted into a subject, an operating unit 22 provided at the proximal end of the insertion unit 21, and a bending portion 23 and a distal portion 24 that are provided at the distal side of the insertion unit 21. By operating an angle knob 22a of the operating unit 22, the bending portion 23 is bent. The distal portion 24 can be directed in a desired direction by the bending operation.

In addition to the angle knob 22a, a freeze button 22b, a zoom operation unit 22c, a mode selector SW (mode selector switch) 22d, and the like are provided in the operating unit 22. The freeze button 22b is a first still image acquisition operation unit for inputting an instruction to acquire a first still image (first still image acquisition instruction) used for re-diagnosis and the like. The zoom operation unit 22c is an imaging magnification change operation unit for inputting an imaging magnification change instruction in order to instruct the imaging optical system to change the imaging magnification. The mode selector SW 22d is a mode switching operation unit for inputting a mode switching instruction for switching between two modes of a normal observation mode (first mode) and a special observation mode (second mode). The normal observation mode is a mode in which the observation target is observed using normal light of white light (or pseudo-white light), and the special observation mode is a mode in which the observation target is observed using special light having a specific wavelength.

The light source device 14 is a device that generates illumination light for irradiating the observation target, and is optically connected to the endoscope 12 by a universal cord 17. The illumination light generated by the light source device 14 is guided by a light guide 41 (refer to FIG. 2) provided in the endoscope 12 and the universal cord 17, and is emitted toward the observation target from the distal portion 24. The light source device 14 is electrically connected to the processor device 16, and adjusts the amount of light or the spectrum of illumination light based on a control signal from the processor device 16.

The processor device 16 is electrically connected to the endoscope 12 by the universal cord 17, and sequentially generates images of the observation target (hereinafter, referred to as observation images) by acquiring image signals from an image sensor 48 (refer to FIG. 2) provided in the distal portion 24. Then, the video of the observation target is displayed on the monitor 18 by sequentially outputting the generated observation images to the monitor 18. The monitor 18 is a display unit that displays information regarding the video of the observation target or the observation image (hereinafter, referred to as an observation image and the like). The console 20 functions as a user interface (UI) for receiving an input operation, such as a function setting.

Figure 2:
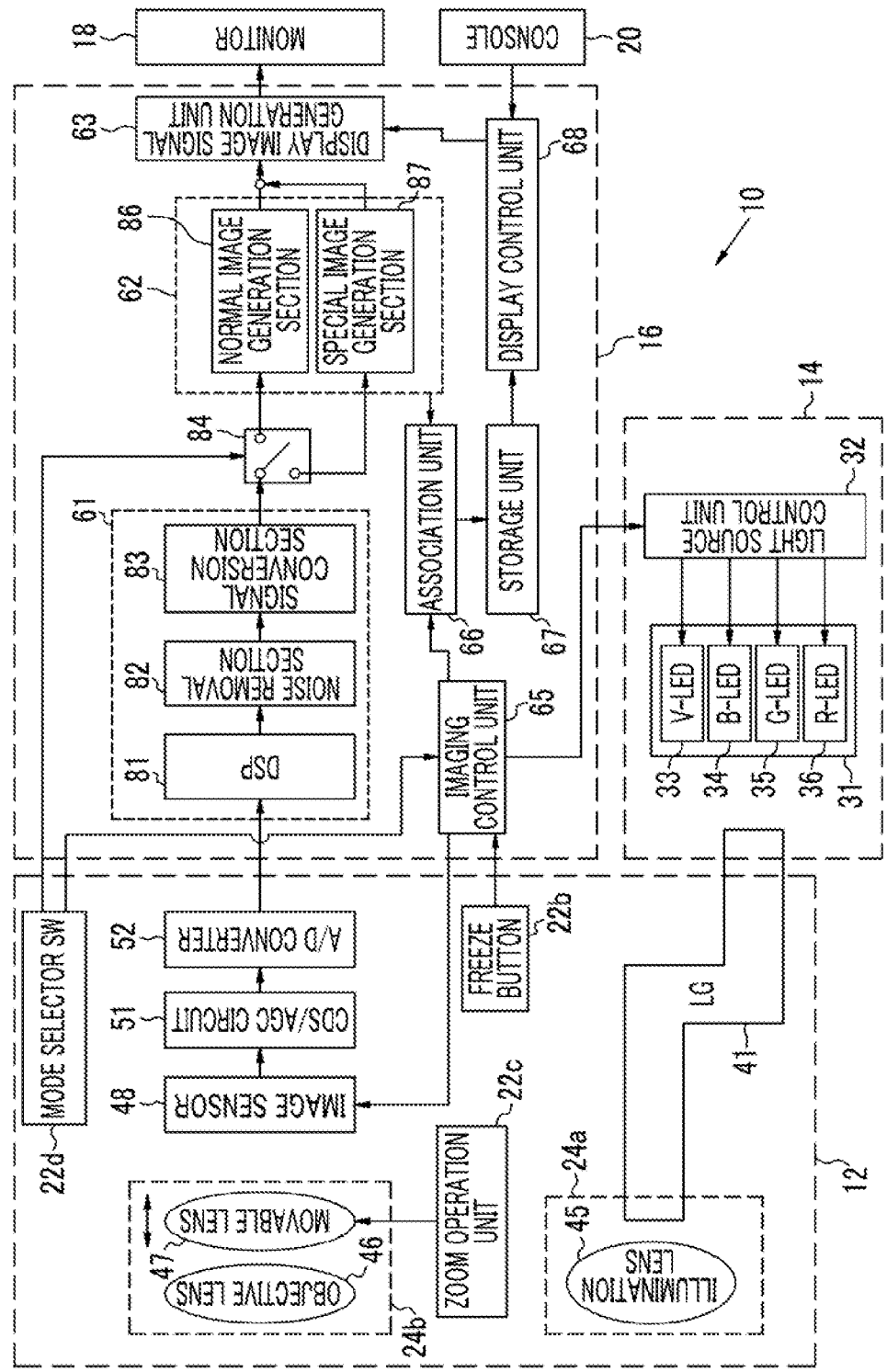
FIG. 2 is a block diagram of the endoscope system.

As shown in FIG. 2, the light source device 14 includes a light emitting diode (LED) light source unit 31 and a light source control unit 32. The LED light source unit 31 includes a violet light emitting diode (V-LED) 33, a blue light emitting diode (B-LED) 34, a green light emitting diode (G-LED) 35, and a red light emitting diode (R-LED) 36 as semiconductor light sources for generating illumination light. ON/OFF of the LEDs 33 to 36 and the amount of emitted light when LEDs 33 to 36 are turned on are independently controlled by the light source control unit 32.

Figure 3:
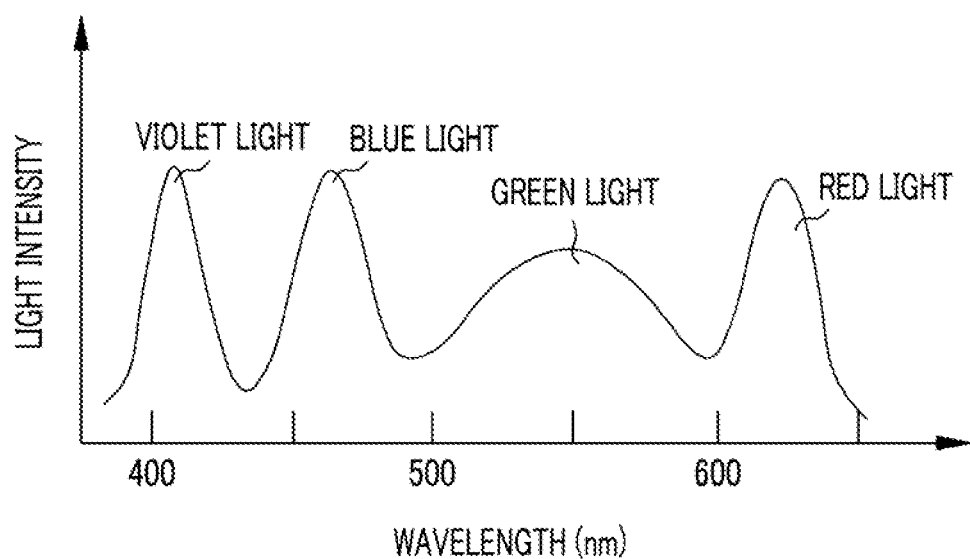
FIG. 3 is a graph showing illumination light in a normal observation mode.

As shown in FIG. 3, the V-LED 33 emits light in a violet wavelength band having a center wavelength of 410 nm to 415 nm (hereinafter, referred to as violet light), and the B-LED 34 emits light in a blue wavelength band having a center wavelength of 445 nm to 460 nm (hereinafter, referred to as blue light). The G-LED 35 emits light in a green wavelength band of about 500 nm to 600 nm (hereinafter, referred to as green light) that is expressed by normal distribution, and the R-LED 35 emits light in a red wavelength band of about 600 nm to 650 nm (hereinafter, referred to as red light). The center wavelength of the red light is about 620 nm to 630 nm.

When the endoscope system 10 is set to the normal observation mode by the mode selector SW 22d, the light source control unit 32 generates normal light of white color by controlling all of the V-LED 33, the B-LED 34, the G-LED 35, and the R-LED 36 to be turned on with the specific amount of emitted light set in advance (refer to FIG. 2). The normal light generated by the LED light source unit 31 is incident on the light guide 41 through optical members such as a condensing lens, an optical fiber, and a multiplexer (not shown), and is guided to an illumination optical system 24a of the distal portion 24. An illumination lens 45 is provided in the illumination optical system 24a, and the normal light guided by the light guide 41 is emitted to the observation target through the illumination lens 45 as illumination light. As a result, in the normal observation mode, the observation target is imaged by the reflected light of the normal light.

Figure 4:
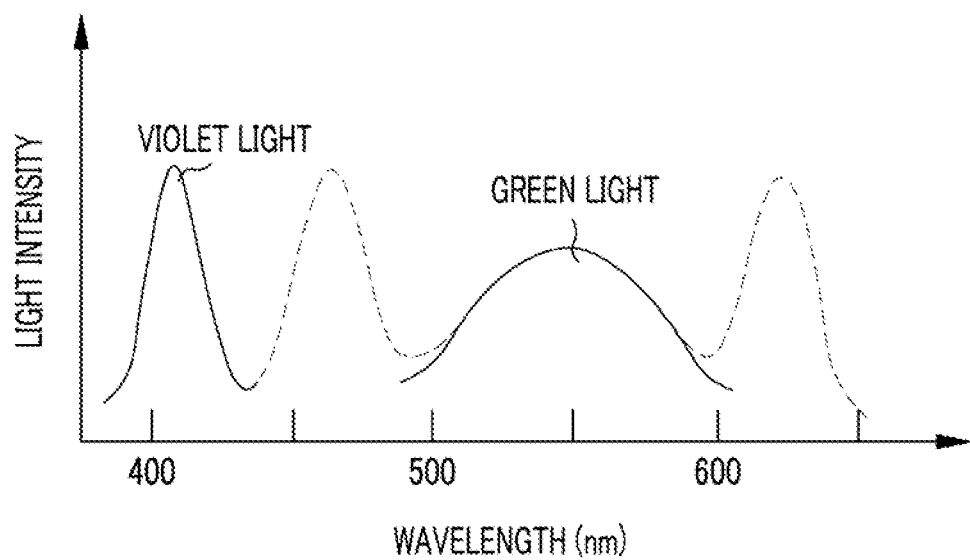
FIG. 4 is a graph showing illumination light in a special observation mode.

On the other hand, when the endoscope system 10 is set to the special observation mode by the mode selector SW 22d, the light source control unit 32 turns on the V-LED 33 and the G-LED 35 and turns off the B-LED 34 and the R-LED 36 in synchronization with the imaging frame of the image sensor 48, as shown in FIG. 4. The violet light and the green light emitted from the V-LED 33 and the G-LED 35 are incident on the light guide 41 through the optical member (not shown), are guided to the illumination optical system 24a, and are emitted to the observation target through the illumination lens 45 as illumination light, in the same manner as in the normal observation mode. As a result, in the special observation mode, the violet light and the green light are emitted to the observation target, and the observation target is imaged by the reflected light of each of the violet light and the green light.

An imaging optical system 24b is provided in the distal portion 24 of the endoscope 12 (refer to FIG. 2). The imaging optical system 24b includes an objective lens 46 and a movable lens 47, and the reflected light of illumination light from the observation target is incident on the image sensor 48 through the objective lens 46 and the movable lens 47. Therefore, an image of the observation target is formed on the image sensor 48. The movable lens 47 is a lens for enlarging or reducing the image of the observation target formed on the image sensor 48, and is moved along the optical axis based on the imaging magnification change instruction that is input to the imaging optical system 24b by operating the zoom operation unit 22c. That is, the imaging magnification of the imaging optical system 24b is variable.

The image sensor 48 images the observation target with the reflected light of illumination light, and outputs an image signal. As the image sensor 48, for example, a charge coupled device (CCD) image sensor or a complementary metal oxide semiconductor (CMOS) image sensor can be used. In addition, the image sensor 48 is a color imaging element, and a blue color filter (hereinafter, referred to as a B filter), a green color filter (hereinafter, referred to as a G filter), or a red color filter (hereinafter, referred to as an R filter) is provided in each pixel.

Figure 5:
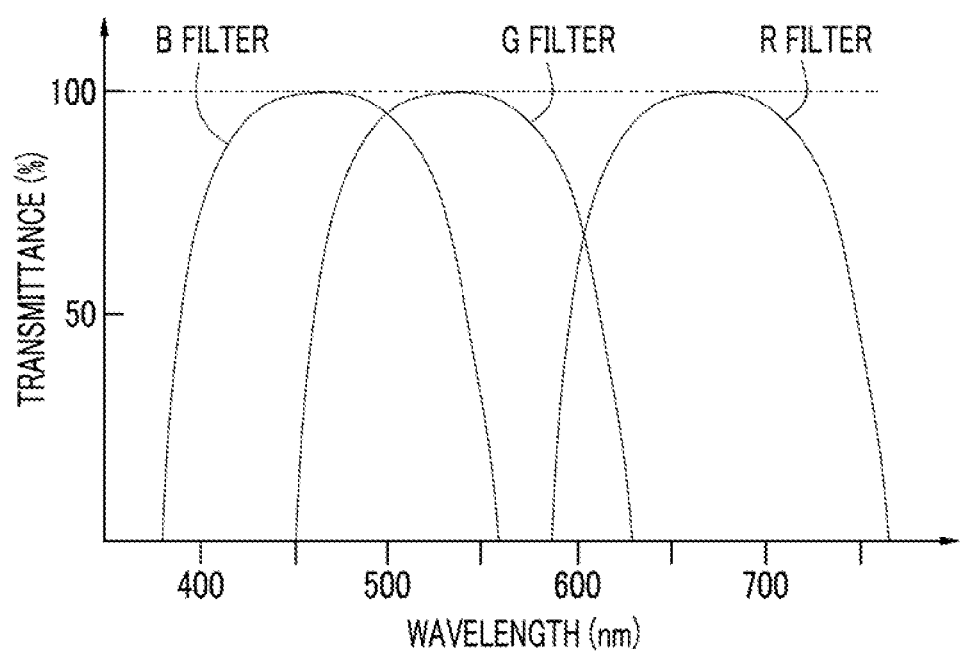
FIG. 5 is a graph showing the spectral transmittance of a color filter.

As shown in FIG. 5, the B filter has a spectral transmittance of 380 nm to 560 nm, the G filter has a spectral transmittance of 450 nm to 630 nm, and the R filter has a spectral transmittance of 580 nm to 760 nm. Accordingly, a B pixel (blue pixel) in which the B filter is provided receives violet light and blue light that are included in the reflected light of the illumination light from the observation target, and outputs a B image signal (blue image signal). Similarly, a G pixel (green pixel) in which the G filter is provided receives green light and outputs a G image signal (green image signal), and an R pixel (red pixel) in which the R filter is provided receives red light and outputs an R image signal (red image signal).

The image signals of the respective colors output from the image sensor 48 are transmitted to a correlated double sampling (CDS)/automatic gain control (AGC) circuit 51. The CDS/AGC circuit 51 performs correlated double sampling (CDS) or automatic gain control (AGC) for the analog image signals output from the image sensor 48. That is, the CDS/AGC circuit 51 functions as a gain control unit that controls a gain when the image sensor 48 outputs image signals. The image signals transmitted through the CDS/AGC circuit 51 are converted into digital image signals by an A/D converter 52. The image signals that have been digitized in this manner are input to the processor device 16.

The processor device 16 includes an image signal acquisition processing unit 61, an image generation unit 62, a display image signal generation unit 63, an imaging control unit (control unit) 65, an association unit 66, a storage unit 67, and a display control unit 68. The image signal acquisition processing unit 61 and the image generation unit 62 form an acquisition unit that acquires an image or a video including two or more images based on the image signal obtained by imaging the observation target with the image sensor 48.

The image signal acquisition processing unit 61 includes a digital signal processor (DSP) 81, a noise removal section 82, and a signal conversion section 83. Using the DSP 81, the noise removal section 82, and the signal conversion section 83, the input of the image signal of each color is received from the image sensor 48, and image signal acquisition processing for acquiring the still image or the video of the observation target is performed.

The DSP 81 functions as a defect correction processing section, an offset processing section, a gain correction processing section, a linear matrix processing section, a gamma conversion processing section, a demosaic processing section, and a YC conversion processing section (none are shown). The defect correction processing section performs defect correction processing for correcting the signal value of a pixel corresponding to a defective pixel of the image sensor 48 on the received image signal of each color.

The offset processing section sets an accurate zero level by excluding a dark current component from the image signal subjected to the defect correction processing. The gain correction processing section adjusts the signal level of each image signal by multiplying the image signal of each color after offset processing by a specific gain. The linear matrix processing section performs linear matrix processing for increasing color reproducibility on the image signal of each color after the gain correction processing. The gamma conversion processing section performs gamma conversion processing for adjusting the brightness or saturation on the image signal after the linear matrix processing. The demosaic processing section generates a signal of missing color in each pixel by interpolation by performing demosaic processing (also referred to as isotropic processing or synchronization processing) on the image signal after the gamma conversion processing. Through the demosaic processing, all pixels have RGB signals. The YC conversion processing section generates a brightness signal Y and color difference signals Cb and Cr by performing YC conversion processing on each image signal after the demosaic processing. The brightness signal Y and the color difference signals Cb and Cr generated by the YC conversion processing section are input to the noise removal section 82.

The noise removal section 82 performs noise removal processing on the input signal using, for example, a moving average method or a median filter method. The respective signals after noise has been removed therefrom are input to the signal conversion section 83, and are reconverted into RGB image signals. Then, the RGB image signals are input to the image generation unit 62 through an image processing switching unit 84.

The image generation unit 62 includes a normal image generation section 86 and a special image generation section 87. Therefore, when the image processing switching unit 84 is set to the normal observation mode by the mode selector SW 22d, the image signal of each color output from the signal conversion section 83 is input to the normal image generation section 86. In addition, when the image processing switching unit 84 is set to the special observation mode by the mode selector SW 22d, the image signal of each color output from the signal conversion section 83 is input to the special image generation section 87.

The normal image generation section 86 generates a normal observation image based on the image signal of each color input from the signal conversion section 83. In the normal observation mode, white normal light is emitted to the observation target. Accordingly, corresponding color information of the observation target is included in the image signal of each color that is output from the signal conversion section 83 in the normal observation mode. For this reason, the normal observation image is generated by assigning the B image signal to the blue pixel, assigning the G image signal to the green pixel, and assigning the R image signal to the red pixel.

The special image generation section 87 generates a special observation image based on the image signal of each color input from the signal conversion section 83. In the special observation mode, violet light and green light are emitted to the observation target. For this reason, the B image signal obtained under violet light and the G image signal obtained under green light, among the image signals of respective colors that are output from the signal conversion section 83 in the special observation mode, include the information of the observation target, and other image signals include little information of the observation target. Therefore, the special image generation section 87 generates a special observation image by assigning the B image signal obtained under violet light to the blue pixel and the green pixel and assigning the G image signal obtained under green light to the red pixel. In the special observation image, for example, a travel pattern, a pit pattern, or the like of a blood vessel near the mucosal surface of the observation target is emphasized.

The normal observation images or the special observation images generated by the image generation unit 62 are sequentially input to the display image signal generation unit 63. The display image signal generation section 63 converts the normal observation image or the special observation image into a display format signal (display image signal; for example, the brightness signal Y and the color difference signals Cb and Cr), and inputs the display format signal to the monitor 18 in a sequential manner. As a result, a video of the observation target formed by the normal observation image (hereinafter, referred to as a normal observation video) or a video of the observation target formed by the special observation image (hereinafter, referred to as a special observation video) is displayed on the monitor 18.

The imaging control unit 65 performs imaging control of the endoscope system 10 by performing overall control of the image sensor 48, the light source control unit 32, and each unit of the endoscope system 10. For example, when a mode switching instruction is received from the mode selector SW 22d, the imaging control unit 65 controls the light source control unit 32 to switch illumination light between normal light (white light) and special light (violet light and green light). In addition, the imaging control unit 65 synchronizes the light emission timing of the illumination light and the imaging frame of the image sensor 48 with each other by inputting a synchronization signal to the light source control unit 32 and the image sensor 48. When the freeze button 22b is pressed, a first still image acquisition instruction is input to the imaging control unit 65. When the first still image acquisition instruction is input, the imaging control unit 65 causes the image signal acquisition processing unit 61 and the image generation unit 62 to acquire a first still image and a video of the observation target before and after the acquisition of the first still image based on the first still image acquisition instruction, and causes the association unit 66 to associate the first still image and the video of the observation target with each other. Then, the first still image and the video of the observation target are stored in the storage unit 67. The storage unit 67 is a non-volatile memory.

Figure 6:
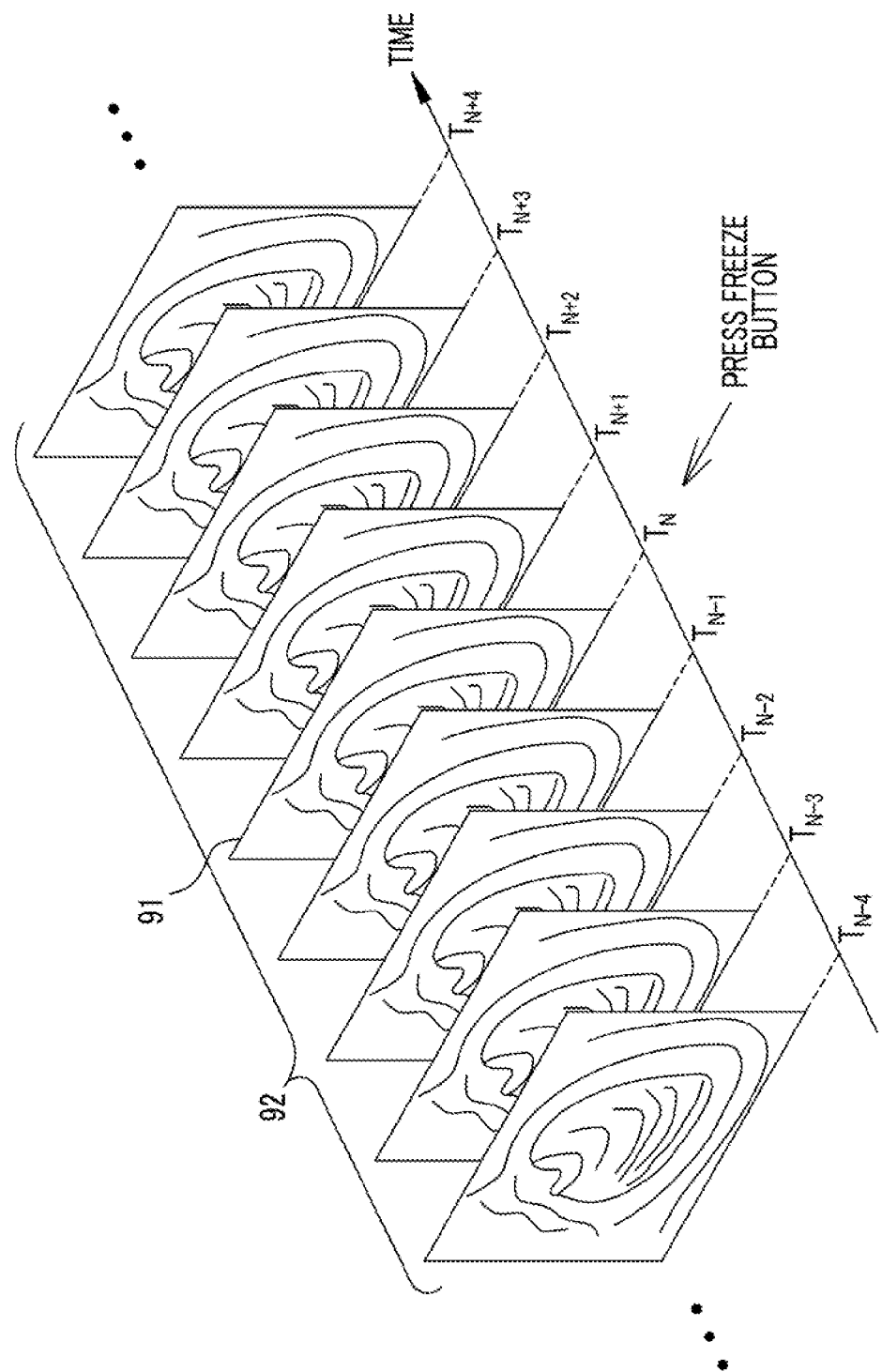
FIG. 6 is an explanatory diagram showing a first still image and the associated video.

The association unit 66 acquires the normal observation image or the special observation image from the image generation unit 62, and stores the normal observation image or the special observation image temporarily by the number of frames set in advance. When the freeze button 22b is pressed and the first still image acquisition instruction is input to the imaging control unit 65, the imaging control unit 65 inputs a storage instruction to the association unit 66. As shown in FIG. 6, in the normal observation mode, it is assumed that the association unit 66 temporarily stores normal observation images of nine or more frames acquired at time $T_{N-4}$ to $T_{N+4}$. In this case, in response to the storage instruction, the association unit 66 stores one normal observation image 91 corresponding to the time (time $T_N$) at which the storage instruction has been received and a normal observation video 92, which is formed by the one normal observation image 91 and normal observation images of, for example, eight frames at time $T_{N-4}$ to $T_{N-1}$ and time $T_{N+1}$ to $T_{N+4}$ acquired before and after the one normal observation image 91, in the storage unit 67 so as to be associated with each other. One normal observation image 91 corresponding to the time at which the storage instruction has been received is the first still image, and the normal observation video 92 formed by normal observation images before and after the one normal observation image is a video associated with the first still image (associated video).

This is the same for the case of the special observation mode. That is, when a storage instruction is received, the association unit 66 stores one special observation image corresponding to the time at which the storage instruction has been received and a video (associated video), which is formed by special observation images before and after the one special observation image, in the storage unit 67 so as to be associated with each other. The first still image and the associated video are associated, for example, by recording information for linking the associated video in the header of the first still image or by recording information for linking the first still image and the associated video to each other in the header of the first still image and the header of the associated video.

Figure 7:
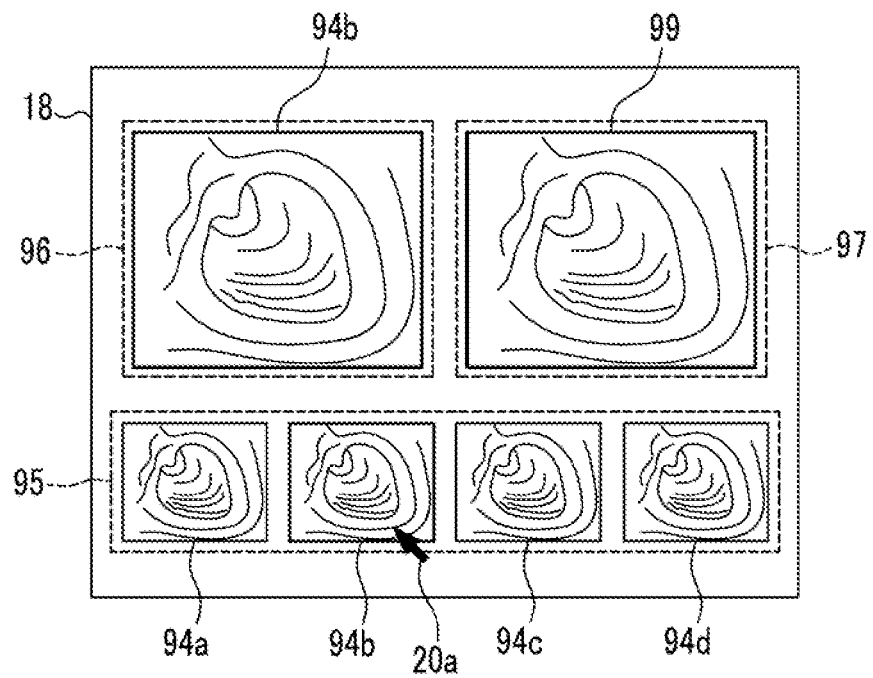
FIG. 7 is an explanatory diagram showing the display of a monitor 18 in a first still image display mode.

The display control unit 68 displays the first still image and the associated video stored in the storage unit 67 on the monitor 18 by reading the first still image and the associated video based on the control signal input from the console 20 and inputting the first still image and the associated video to the display image signal generation unit 63. More specifically, when switching the processor device 16 from a first processing mode for observing the observation target in real time to a first still image display mode for re-diagnosis and the like, in which the first still image is read from the storage unit 67 and is displayed on the monitor 18, using the console 20, the display control unit 68 reads a plurality of first still images 94a to 94d stored in the storage unit 67, and displays the first still image 94a to 94d side by side in a reduced display portion 95 set on the monitor 18 so as to be reduced, as shown in FIG. 7.

In addition, an enlarged display portion 96, in which the selected first still image is enlarged and displayed so that the selected first still image is larger than in the reduced display portion 95 when one of the first still images 94a to 94d displayed in the reduced display portion 95 is selected, and an associated display portion 97, in which an associated video associated with the selected first still image is reproduced, are set on the monitor 18. When one (for example, the first still image 94b) of the first still images 94a to 94d in the reduced display portion 95 is selected by a cursor 20a (selection unit) for selecting the first still image in response to the operation of the console 20, the display control unit 68 enlarges and displays the selected first still image in the enlarged display portion 96, and reads an associated video 99 associated with the selected first still image from the storage unit 67 and displays (reproduces) the associated video 99 in the associated display portion 97.

In the present embodiment, the first still images are displayed side by side in the reduced display portion 95. However, the first still images displayed side by side do not necessarily need to be reduced. First still images that are not reduced images may be displayed on the monitor 18 side by side and an associated video may be displayed in the associated display portion 97 when one of the first still images is selected.

Figure 8:
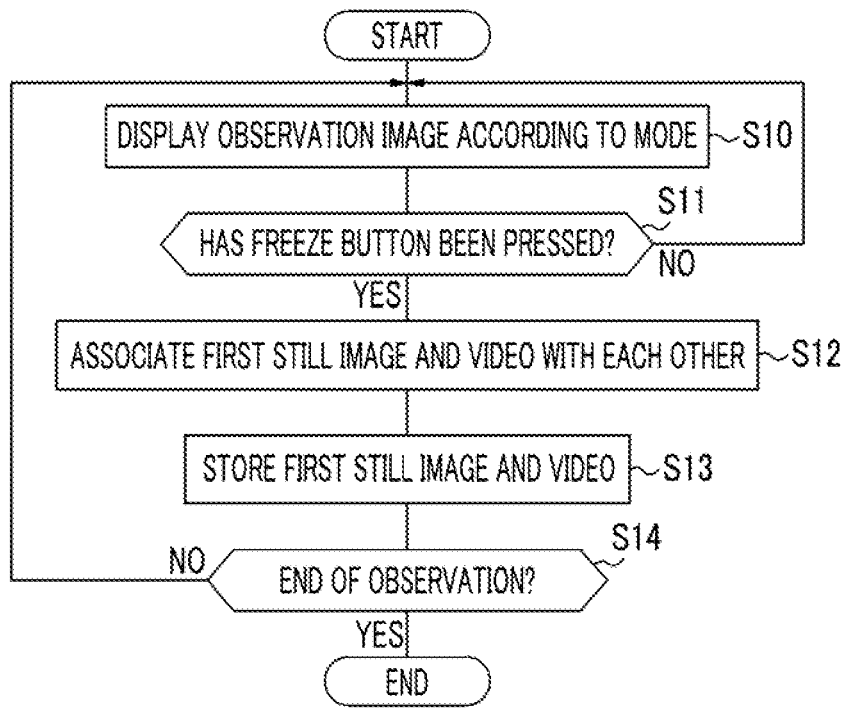
FIG. 8 is a flowchart showing the operation when performing real-time diagnosis.

Next, the operation when performing real-time observation in the endoscope system 10 according to the present embodiment will be described with reference to FIG. 8. When the insertion unit 21 of the endoscope 12 is inserted into the subject, the observation target is imaged according to the mode selected by the mode selector SW 22d, and observation images generated based on the image signal output from the image sensor 48 and an observation video formed from the observation images are acquired and are displayed on the monitor 18 (S10: acquisition step). For example, when the normal observation mode is set by the mode selector SW 22d, the imaging control unit 65 controls the light source control unit 32 to generate white normal light as illumination light from the LED light source unit 31. Therefore, the image sensor 48 images the observation target under normal light, and normal observation images are generated by the normal image generation section 86. The normal observation images are sequentially displayed on the monitor 18 by being converted into display image signals by the display image signal generation unit 63. As a result, in the normal observation mode, a normal observation video is displayed on the monitor 18. In addition, normal observation images that form the frames of the normal observation video displayed on the monitor 18 as described above are temporarily stored by the number of frames set in advance in the association unit 66.

Then, when the freeze button 22b is pressed and the first still image acquisition instruction is input to the imaging control unit 65 (S11: YES), the imaging control unit 65 inputs a storage instruction to the association unit 66. When the storage instruction is input from the imaging control unit 65, the association unit 66 associates a normal observation image corresponding to the input time of the first still image acquisition instruction, among the plurality of normal observation videos that are temporarily stored, with a normal observation video formed from normal observation images acquired before and after the normal observation image (S12: association step), and automatically stores the normal observation image, that is a still image, in the storage unit 67 as a first still image for re-diagnosis and the like and automatically stores the normal observation video in the storage unit 67 as a video associated with the first still image (S13: storage step). These operations are repeated whenever the freeze button 22b is pressed until the real-time observation ends (S14). This is the same for the case of the special observation mode.

Figure 9:
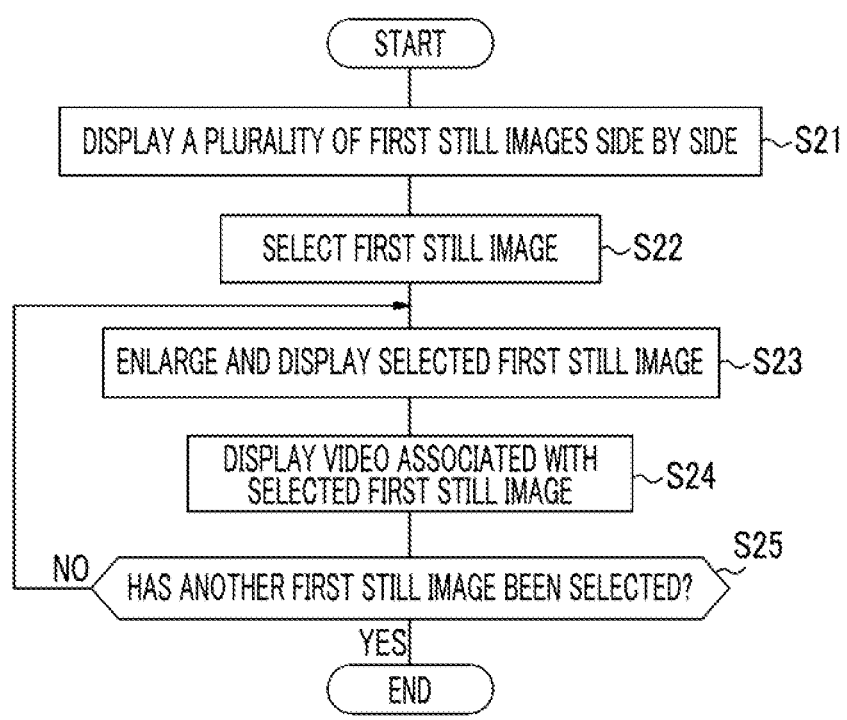

When using the first still image stored in the storage unit 67, the processor device 16 is switched to the first still image display mode by operating the console 20. In this case, as shown in FIG. 9, the display control unit 68 reads a plurality of first still images 94a to 94d stored in the storage unit 67 and displays the plurality of first still images 94a to 94d side by side in the reduced display portion 95 (S21; refer to FIG. 7). Then, when the console 20 is operated to select one of the first still image 94a to 94d displayed in the reduced display portion 95 with the cursor 20a (S22), the display control unit 68 enlarges and displays the selected first still image in the enlarged display portion 96 (S23), and reads an associated video associated with the selected first still image from the storage unit 67 and displays the associated video in the associated display portion 97 (S24). Then, when another first still image is newly selected in the reduced display portion 95, the newly selected first still image is displayed in the enlarged display portion 96 and an associated video is displayed in the associated display portion 97 in the same manner as described above (S25).

As described above, the endoscope system 10 automatically acquires a video associated with a first still image used for re-diagnosis and the like in addition to the first still image, and stores these so as to be associated with each other. Therefore, when performing re-diagnosis and the like, it is possible to support the re-diagnosis and the like by supplying not only the first still image but also the video associated with the first still image. In addition, since the complexity of mode switching is reduced, operability for storing a still image or a video for re-diagnosis and the like is improved. In addition, since the efficiency of real-time diagnosis and re-diagnosis and the like is increased, it is possible to prevent human mistakes, such as oversight.

Figure 10:
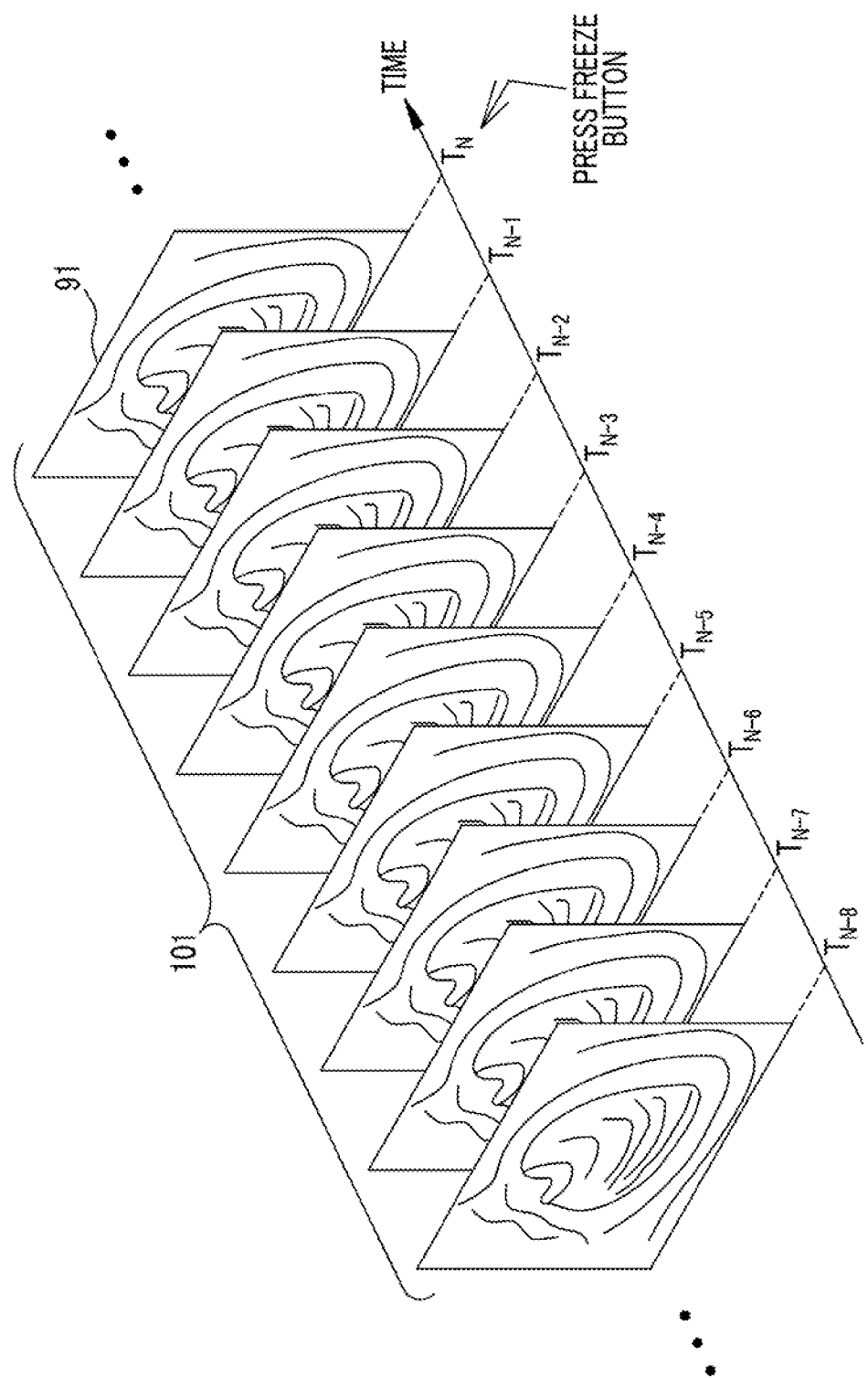
FIG. 10 is an explanatory diagram showing an example in which a video formed by images acquired before the acquisition of a first still image is stored so as to be associated with the first still image.

In the first embodiment described above, in the normal observation mode, when the normal observation image 91 corresponding to the pressing time (time $T_N$) of the freeze button 22b is stored in the storage unit 67 as a first still image, a normal observation video formed by the normal observation image 91, normal observation images at time $T_{N-4}$ to $T_{N-1}$ before the acquisition of the normal observation image 91, and normal observation images at time $T_{N+1}$ to $T_{N+4}$ after the acquisition of the normal observation image 91 are stored in the storage unit 67 so as to be associated with the normal observation image 91 that is a first still image. However, as shown in FIG. 10, a normal observation video 101 formed by the normal observation image 91 at the pressing time (time $T_N$) of the freeze button 22b and normal observation images acquired at time $T_{N-8}$ to $T_{N-1}$ before the acquisition of the normal observation image 91 may be stored in the storage unit 67 so as to be associated with the normal observation image 91 that is a first still image. In this case, a normal observation video formed by the normal observation images acquired at time $T_{N-8}$ to $T_{N-1}$ before the acquisition of the normal observation image 91 without including the normal observation image 91 may be stored in the storage unit 67 so as to be associated with the normal observation image 91 that is a first still image.

Figure 11:
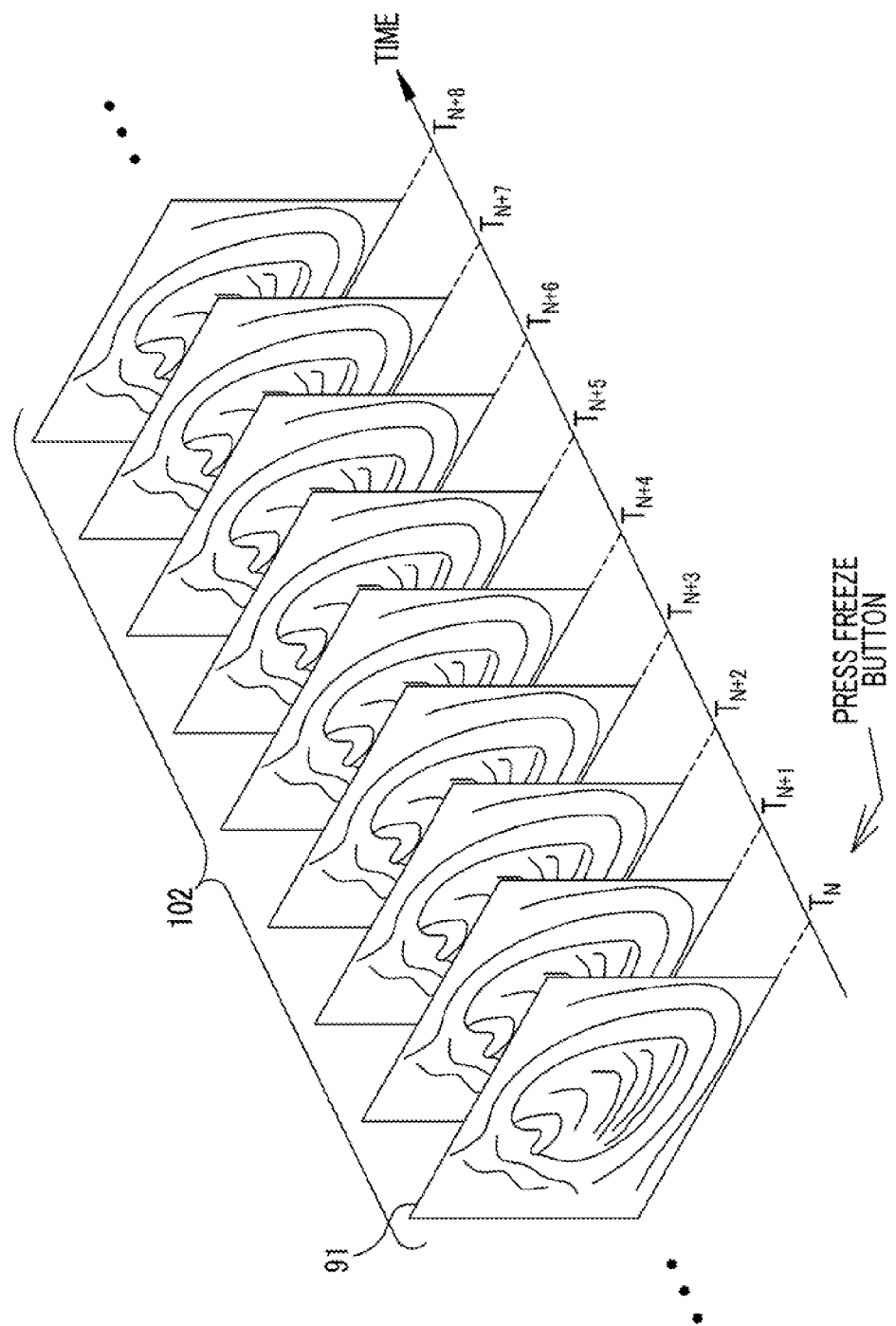
FIG. 11 is an explanatory diagram showing an example in which a video formed by images acquired after the acquisition of a first still image is stored so as to be associated with the first still image.

On the contrary, as shown in FIG. 11, a normal observation video 102 formed by the normal observation image 91 at the pressing time (time $T_N$) of the freeze button 22b and normal observation images acquired at time $T_{N+1}$ to $T_{N+8}$ after the acquisition of the normal observation image 91 may be stored in the storage unit 67 so as to be associated with the normal observation image 91 that is a first still image. Needless to say, a normal observation video formed by the normal observation images acquired at time $T_{N+1}$ to $T_{N+8}$ before the acquisition of the normal observation image 91 without including the normal observation image 91 may be stored in the storage unit 67 so as to be associated with the normal observation image 91 that is a first still image. These are the same for the case of the special observation mode.

That is, each of videos before and after the acquisition of a first still image, which are automatically stored so as to be associated with the first still image for the sake of re-diagnosis and the like, is any of a video formed by images of a plurality of frames including the first still image therebetween, a video formed by images acquired before the acquisition of the first still image (or before the first still image), and a video formed by images acquired after the acquisition of the first still image (or after the first still image).

In addition, it is preferable that an associated video, which is stored so as to be associated with the first still image, is formed by images of at least two frames. When the associated video includes a first still image, it is preferable that the association unit 66 associates information for determining the position of the first still image (hereinafter, referred to as position information) in the associated video with at least one of the first still image and the associated video. For example, the association unit 66 records position information, which indicates which frame of the associated video corresponds to the first still image, on the header of the first still image and the header of the associated video. Thus, if the position information of the first still image in the associated video is recorded, when reproducing the associated video on the monitor 18, the display control unit 68 can notify of a frame corresponding to the first still image in the associated video by performing a temporary stop at the frame corresponding to the first still image, or lightening the frame corresponding to the first still image (lightening the frame corresponding to the first still image only for a moment so that it can be seen that the frame corresponding to the first still image is a frame that has been frozen), or superimposing a message on the frame corresponding to the first still image, for example, based on the recorded position information.

In the first embodiment described above, the freeze button 22b is pressed and the first still image and the associated video are stored in the storage unit 67 so as to be associated with each other, and both of the first still image and the associated video are acquired in the same mode. However, when a video formed by images acquired after the acquisition of the first still image is stored so as to be associated with the first still image, the associated video may be formed by images acquired in a different mode from the first still image.

Figure 12:
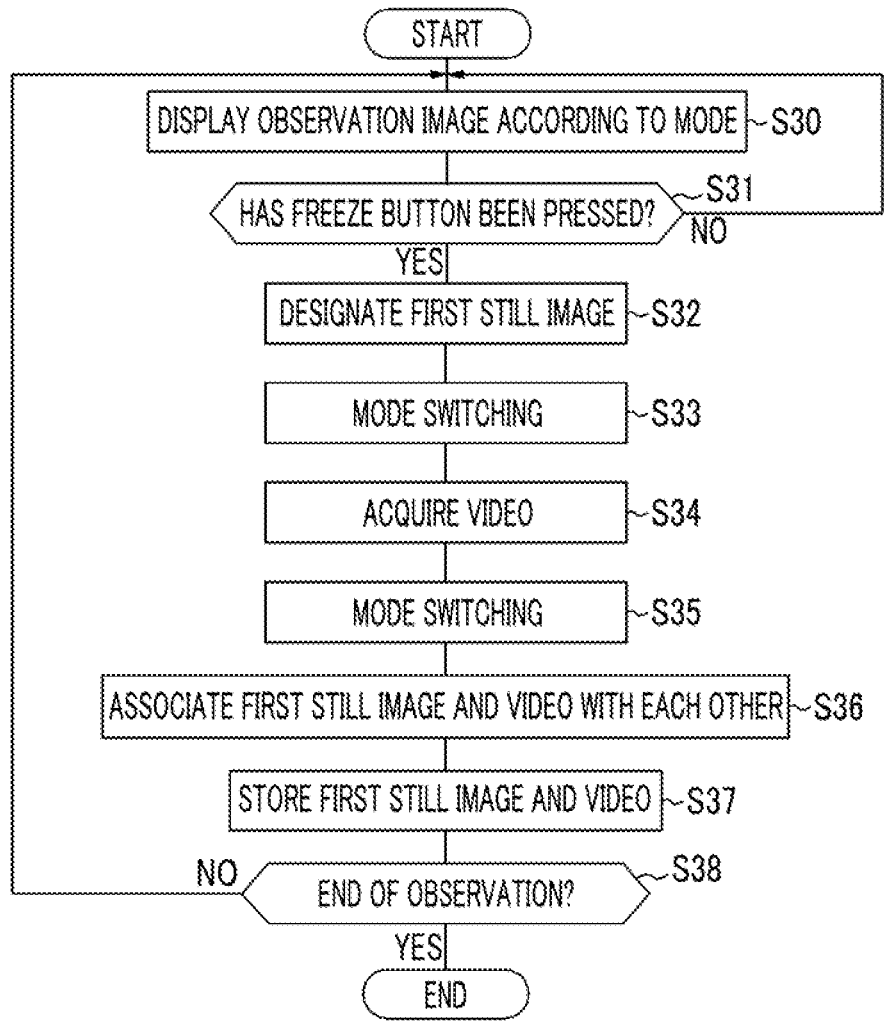
FIG. 12 is a flowchart when acquiring an associated video in a different mode from the first still image.

In this case, as shown in FIG. 12, when displaying the observation video on the monitor 18 in a mode set by the mode selector SW 22d (S30), if the freeze button 22b is pressed (S31), the imaging control unit 65 inputs a storage instruction to the association unit 66 to designate a first still image corresponding to the pressing time of the freeze button 22b (S32). Then, the imaging control unit 65 controls the light source control unit 32 and the image processing switching unit 84 regardless of the mode switching instruction from the mode selector SW 22d, thereby switching the observation mode from the mode set first to another mode (S33). Then, the association unit 66 acquires observation images of frames set in advance in the mode after switching (S34). As a result, a video in a different mode from the mode that has been set when pressing the freeze button 22b is stored in the association unit 66. After the observation images of the frames set in advance are acquired in the different mode from the mode that has been set when pressing the freeze button 22b, the imaging control unit 65 controls the light source control unit 32 and the image processing switching unit 84 to switch back to the mode that has been set when pressing the freeze button 22b (S35). When a notification indicating that mode switching to the original mode when pressing the freeze button 22b has been performed is received from the imaging control unit 65, the association unit 66 associates a first still image corresponding to the pressing time of the freeze button 22b with an observation video formed by images acquired after mode switching is forcibly performed by the imaging control unit 65 (S36), and stores the first still image and the observation video in the storage unit 67 (S37). Then, the above operation is repeated until the end of the observation (S38).

In this manner, for example, when the normal observation mode is set, a first still image in the normal observation mode and an associated video in the special observation mode are associated with each other and are automatically stored in the storage unit 67. On the contrary, when the special observation mode is set, a first still image in the special observation mode and an associated video in the normal observation mode are associated with each other and are automatically stored in the storage unit 67. By acquiring the first still image and the associated video in different modes as described above, the features of the observation target that are difficult to observe in the first still image can be clearly observed in the associated video. This is helpful for re-diagnosis and the like.

In the modification example described above, in response to the pressing of the freeze button 22b, the first still image for re-diagnosis and the like and each of the videos before and after the acquisition of the first still image are acquired in different modes, are associated, and are stored. However, a still image (second still image) may be automatically acquired in a different mode from the first still image, and the first still image and the second still image may be stored in the storage unit 67 so as to be associated with each other. This can be realized by performing mode switching by one frame after the instruction of the first still image in the modification example described above.

Second Embodiment

Figure 13:
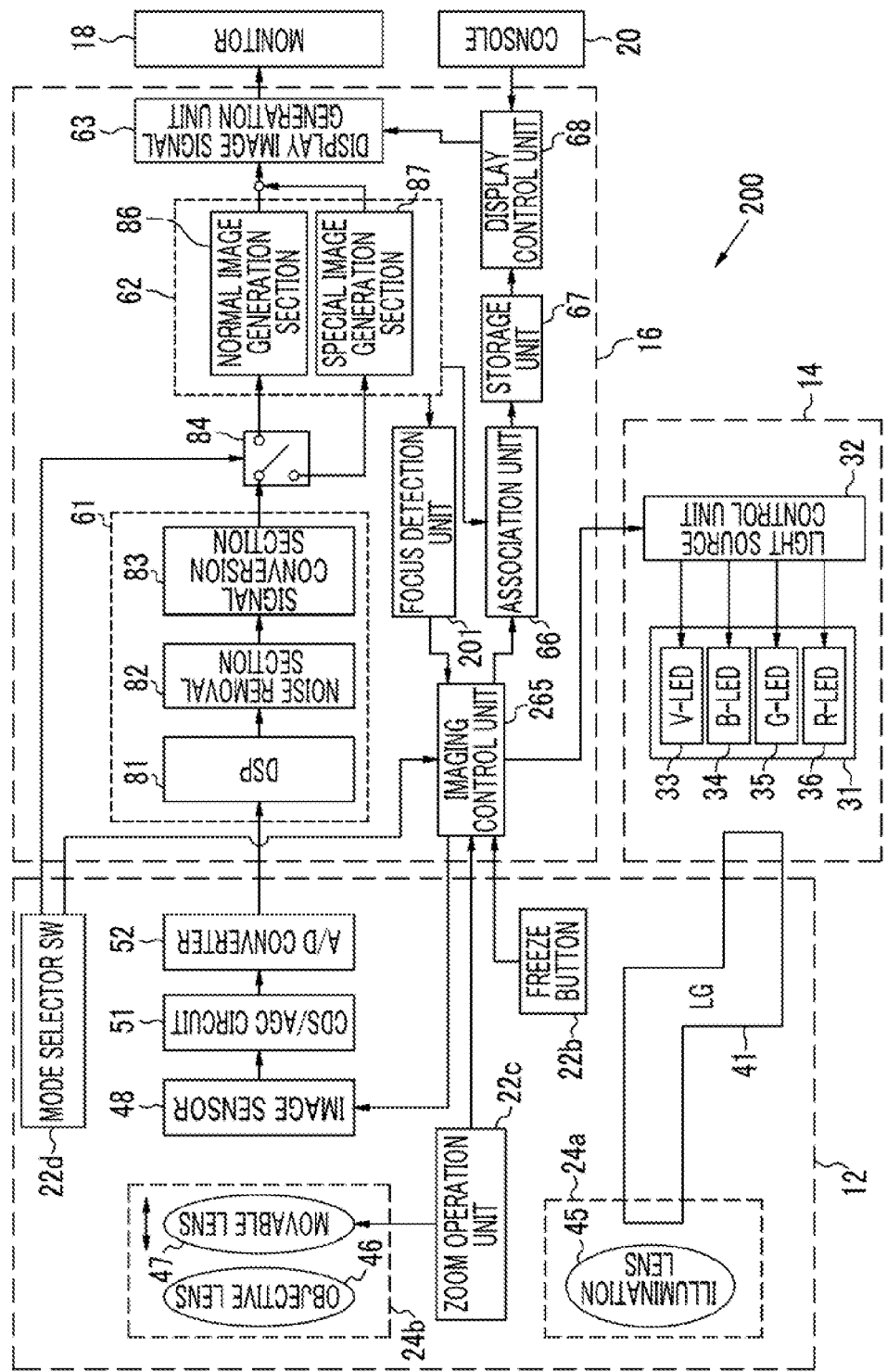
FIG. 13 is a block diagram of an endoscope system according to a second embodiment.

As shown in FIG. 13, in an endoscope system 200 according to a second embodiment, a focus detection unit 201 is added to the endoscope system 10 according to the first embodiment. In addition, instead of the imaging control unit 65, an imaging control unit 265 that operates based on the imaging magnification change instruction input not only from the freeze button 22b but also from the zoom operation unit 22c is provided in the endoscope system 200 according to the second embodiment. The endoscope system 200 according to the second embodiment is the same as the endoscope system 10 according to the first embodiment except for those described above.

The focus detection unit 201 acquires a normal observation image or a special observation image from the image generation unit 62, and detects whether or not the image is in focus. When the focus matches predetermined criteria or more, a focus pass signal is input to the imaging control unit 265.

The operation of the imaging control unit 265 when the freeze button 22b is pressed is the same as that of the imaging control unit 65 in the first embodiment. On the other hand, the imaging control unit 265 monitors the operation of the zoom operation unit 22c, and acquires an imaging magnification change instruction for controlling the movable lens 47 from the zoom operation unit 22c. Then, when the operation of the zoom operation unit 22c is detected after acquiring the imaging magnification change instruction, the imaging control unit 265 inputs a first still image instruction signal, which designates a first still image corresponding to the operation time of the zoom operation unit 22c, to the association unit 66. As a result, at least an image when the operation of the zoom operation unit 22c is started is stored in the storage unit 67 as a first still image.

In addition, the imaging control unit 265 determines whether the imaging magnification change instruction is zoom-in to increase the imaging magnification or zoom-out to reduce the imaging magnification. When the acquired imaging magnification change instruction is zoom-in, a storage instruction is input to the association unit 66 when a focus pass signal is input from the focus detection unit 201. When a zoom-in operation has been performed in response to the imaging magnification change instruction, an observation image when the observation image is in focus for the first time is designated as a second still image after the operation start of the zoom operation unit 22c. After the second still image is designated in this manner, the association unit 66 stores the first still image and the second still image in the storage unit 67 so as to be associated with each other.

On the other hand, when the acquired imaging magnification change instruction is zoom-out, the imaging control unit 265 detects the input end of the imaging magnification change instruction of the zoom operation unit 22c, that is, the operation end of the zoom operation unit 22c. Then, when the operation end of the zoom operation unit 22c is detected, a storage instruction is input to the association unit 66. When a zoom-out operation has been performed in response to the imaging magnification change instruction, an observation image corresponding to the operation end time of the zoom operation unit 22c is designated as a second still image. After the second still image is designated in this manner, the association unit 66 stores the first still image and the second still image in the storage unit 67 so as to be associated with each other, in the same manner as at the time of zoom-in.

Figure 14:
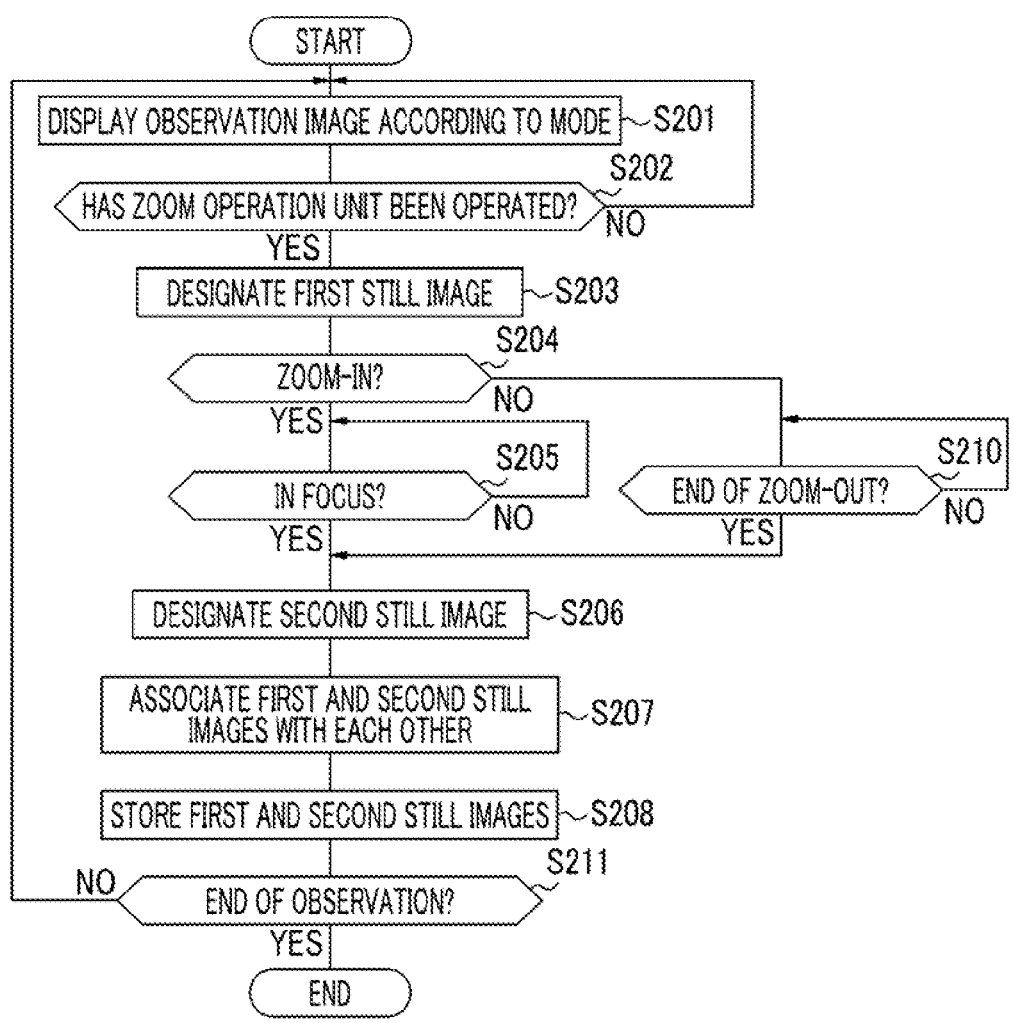
FIG. 14 is a flowchart showing the operation in the second embodiment.

In the endoscope system 200 configured as described above, as shown in FIG. 14, when an observation video corresponding to the mode set by the mode selector SW 22d is displayed on the monitor 18 (S201) and the zoom operation unit 22c is operated (S202), an observation image corresponding to the operation start of the zoom operation unit 22c is automatically designated as a first still image for re-diagnosis and the like even if the freeze button 22b is not pressed (S203). In addition, the imaging control unit 265 designates a first still image or an observation image, which is acquired from the frame after the first still image, as a start frame of a video in a step of designating the first still image. Then, the acquisition of a video, which will become an associated video later, is started.

When the operation of the zoom operation unit 22c is a zoom-in operation (S204: YES), the imaging control unit 265 waits for the input of a focus pass signal from the focus detection unit 201 in order to detect whether or not an observation image is in focus (S205). When an observation image is in focus and the focus pass signal is input to the imaging control unit 265, the imaging control unit 265 starts the start of zoom-in by inputting a storage instruction to the association unit 66, and designates an observation image corresponding to the time when the observation image is in focus for the first time as a second still image (S206). At the time of zoom-in, the association unit 66 associates a first still image corresponding to the start of zoom-in with a second still image corresponding to the time when an observation image is in focus for the first time after the start of zoom-in (S207), and stores these in the storage unit 67 (S208).

On the other hand, when the operation of the zoom operation unit 22c is zoom-out (S204: NO), the imaging control unit 265 waits for the input end of the imaging magnification change instruction from the zoom operation unit 22c (S210). That is, when the imaging magnification change instruction from the zoom operation unit 22c is stopped and the end of the zoom operation is detected or when it is detected that the imaging magnification change instruction indicating the minimum imaging magnification is continuously input (hereinafter, referred to as an end of zoom-out), the imaging control unit 265 inputs a storage instruction to the association unit 66 and designates a second still image corresponding to the end of zoom-out (S206). Then, the association unit 66 associates the first still image corresponding to the start of zoom-out with the second still image corresponding to the end of zoom-out (S207), and stores these in the storage unit 67 (S208). In the endoscope system 200, the operation according to such an operation of the zoom operation unit 22c is repeated until the end of the observation (S211).

In addition, when the freeze button 22b is pressed, the endoscope system 200 according to the second embodiment operates in the same manner as the endoscope system 10 according to the first embodiment. Also in the endoscope system 200 according to the second embodiment, the operation when displaying the first and second still images, which are stored in the storage unit 67 so as to be associated with each other, on the monitor 18 for re-diagnosis and the like is the same as that of the processor device 16 in the first embodiment. That is, in the endoscope system 200, the display control unit 68 displays the first still images stored in the storage unit 67 side by side in the reduced display portion 95 regardless of whether the first still images has been acquired in response to the pressing of the freeze button 22b or the first still images has been acquired in response to the operation of the zoom operation unit 22c (refer to FIG. 7). When one of the first still images displayed in the reduced display portion 95 is selected by the operation using the console 20, if the selected first still image is a first still image acquired in response to the operation of the zoom operation unit 22c, the selected first still image is enlarged and displayed in the enlarged display portion 96, and the second still image that is stored in the storage unit 67 so as to be associated with the selected first still image is displayed in the associated display portion 97.

As described above, when the freeze button 22b is pressed, the endoscope system 200 according to the second embodiment operates in the same manner as the endoscope system 10 according to the first embodiment. In addition, when the zoom operation unit 22c is operated, the first and second still image for re-diagnosis and the like are automatically stored in the storage unit 67 even if the freeze button 22b is not pressed. The zoom operation unit 22c is operated mainly when there is a lesion or tissue suspected as a lesion in the field of view. Accordingly, still images before and after the operation of the zoom operation unit 22c may be a distant-view image of the lesion or the like and an enlarged image of the lesion. In the endoscope system 200, by automatically storing the first and second still images so as to be associated with each other in response to the operation of the zoom operation unit 22c, a distant-view image and a near-view image of the location that the doctor suspects as a lesion can be presented when performing re-diagnosis and the like even if the freeze button 22b is not pressed (or even if the user forgets to press). Therefore, it is possible to support re-diagnosis and the like. In addition, in the endoscope system 200 according to the second embodiment, it is easy to acquire a still image when changing the imaging magnification by which it is difficult to perform imaging.

Figure 15:
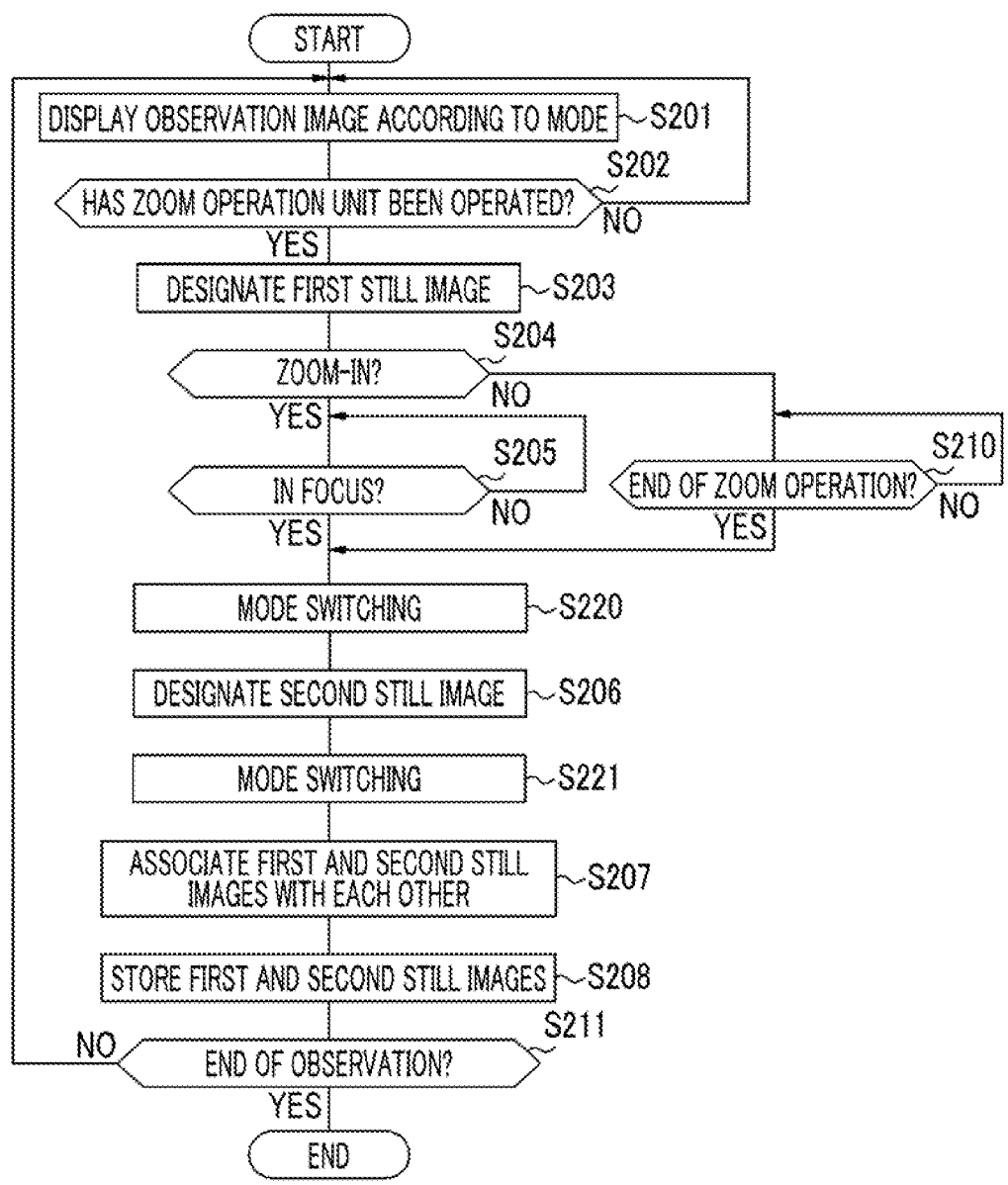
FIG. 15 is a flowchart when acquiring a second still image in a different mode from the first still image.

Also in the endoscope system 200 according to the second embodiment, the second still image may be acquired in a different mode from the first still image, as in the modification example (refer to FIG. 12) of the endoscope system 10 according to the first embodiment. In this case, as shown in FIG. 15, before step S206 of designating the second still image, the imaging control unit 265 may perform a mode change to a different mode from the mode at the time of designation of the first still image (S203) by controlling the light source control unit 32 and the image generation unit 62 (S220). The second still image may be acquired and designated in the mode after the change (S206), and then the changed mode may return to the same mode as the mode at the start of the operation of the zoom operation unit 22c (S202) (S221). In this manner, also in the endoscope system 200, it is possible to acquire the first and second still images in different modes.

Figure 16:
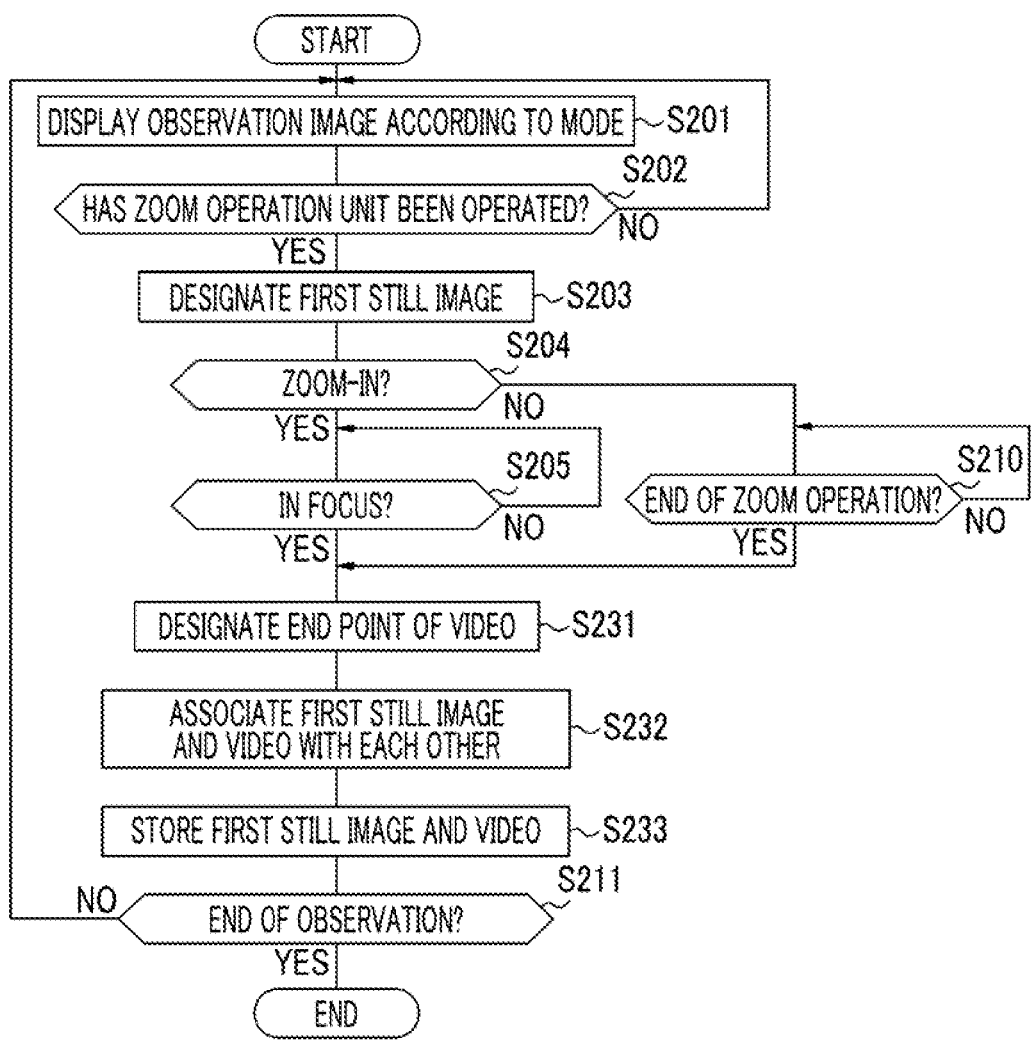
FIG. 16 is a flowchart when storing a first still image and an associated video so as to be associated with each other in response to the operation of a zoom operation unit.

In the endoscope system 200 according to the second embodiment, the first still image corresponding to the start of the operation of the zoom operation unit 22c and the second still image are stored in the storage unit 67 so as to be associated with each other. However, as in the endoscope system 10 according to the first embodiment, the first still image and the video may be stored in the storage unit 67 so as to be associated with each other. In this case, as shown in FIG. 16, the imaging control unit 265 inputs an end point designation signal for designating the end point of the video to the association unit 66 instead of step S206 of designating the second still image (S231). When the end point designation signal is received, the association unit 66 may associate an associated video, which is formed by images of the first still image (or the next frame of the first still image) to a frame corresponding to the end point designation signal, with the designated first still image (S232), and store these in the storage unit 67 (S233).

Figure 17:
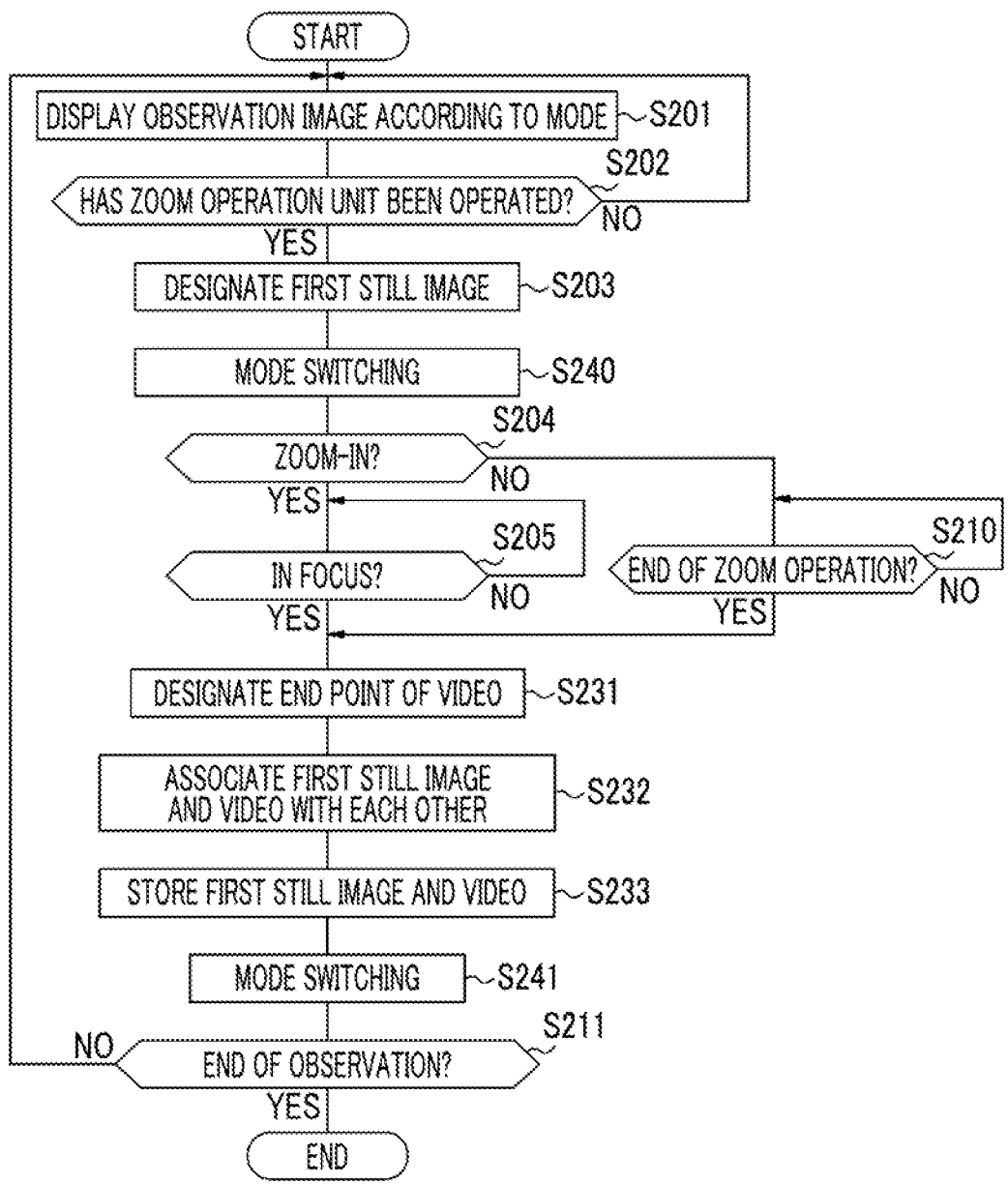
FIG. 17 is a flowchart when storing a first still image and the associated video so as to be associated with each other in response to the operation of the zoom operation unit and acquiring the first still image and the associated video in different modes.

When the first still image and the associated video are stored in the storage unit 67 so as to be associated with each other as described above, the first still image and the associated video may be acquired in different modes. In this case, as shown in FIG. 17, the imaging control unit 265 controls the light source control unit 32 and the image generation unit 62 after designating the first still image (S203), thereby performing a change to a different mode from the mode at the time of designation of the first still image (S240). Then, in frames after an image designated as the first still image, observation images in a different mode from the first still image are sequentially stored in the association unit 66. Accordingly, the associated video formed by the images up to the frame corresponding to the end point designation signal as described above is associated with the designated first still image (S232), and the designated first still image and the associated video are stored in the storage unit 67 (S233). Then, the light source control unit 32 and the image generation unit 62 are controlled again to return to the same mode as the mode at the time of designation of the first still image (S241).

The second embodiment and the modification example are particularly useful for an endoscope system in which the position of the movable lens 47 is controlled smoothly (or in a plurality of steps) based on the imaging magnification change instruction input from the zoom operation unit 22c. However, the invention is also suitable for an endoscope system including an imaging optical system in which the position of the movable lens 47 is controlled in two steps between the first position (for example, a position for reducing the image of the observation target in the minimum scale) and the second position (for example, a position for enlarging the image of the observation target with respect to the first position). Also in the endoscope system including the imaging optical system in which the position control of the movable lens 47 is performed in two steps, when the imaging magnification change instruction is input to the imaging control unit 265 by the operation of the zoom operation unit 22c, the observation image corresponding to the operation time of the zoom operation unit 22c is set as the first still image in the same manner as in the second embodiment and the modification example.

On the other hand, in the second embodiment described above, when the imaging magnification change instruction that is a zoom-in instruction is input to the imaging control unit 265, an observation image when the observation image is in focus for the first time after the start of the operation of the zoom operation unit 22c is set as the second still image. In contrast, in the endoscope system including the imaging optical system in which the position control of the movable lens 47 is performed in two steps, when the imaging magnification change instruction that is a zoom-in instruction for changing the position of the movable lens 47 from the first position to the second position is input to the imaging control unit 265, an observation image corresponding to the time when the position of the movable lens 47 is changed to the second position may be set as the second still image. Also in the case where the imaging magnification change instruction that is a zoom-out instruction for changing the position of the movable lens 47 from the second position to the first position is input to the imaging control unit 265, an observation image corresponding to the time when the position of the movable lens 47 is changed to the first position may be similarly set as the second still image. This is also the same for the case where the first and second still images are acquired in different observation modes.

Figure 18:
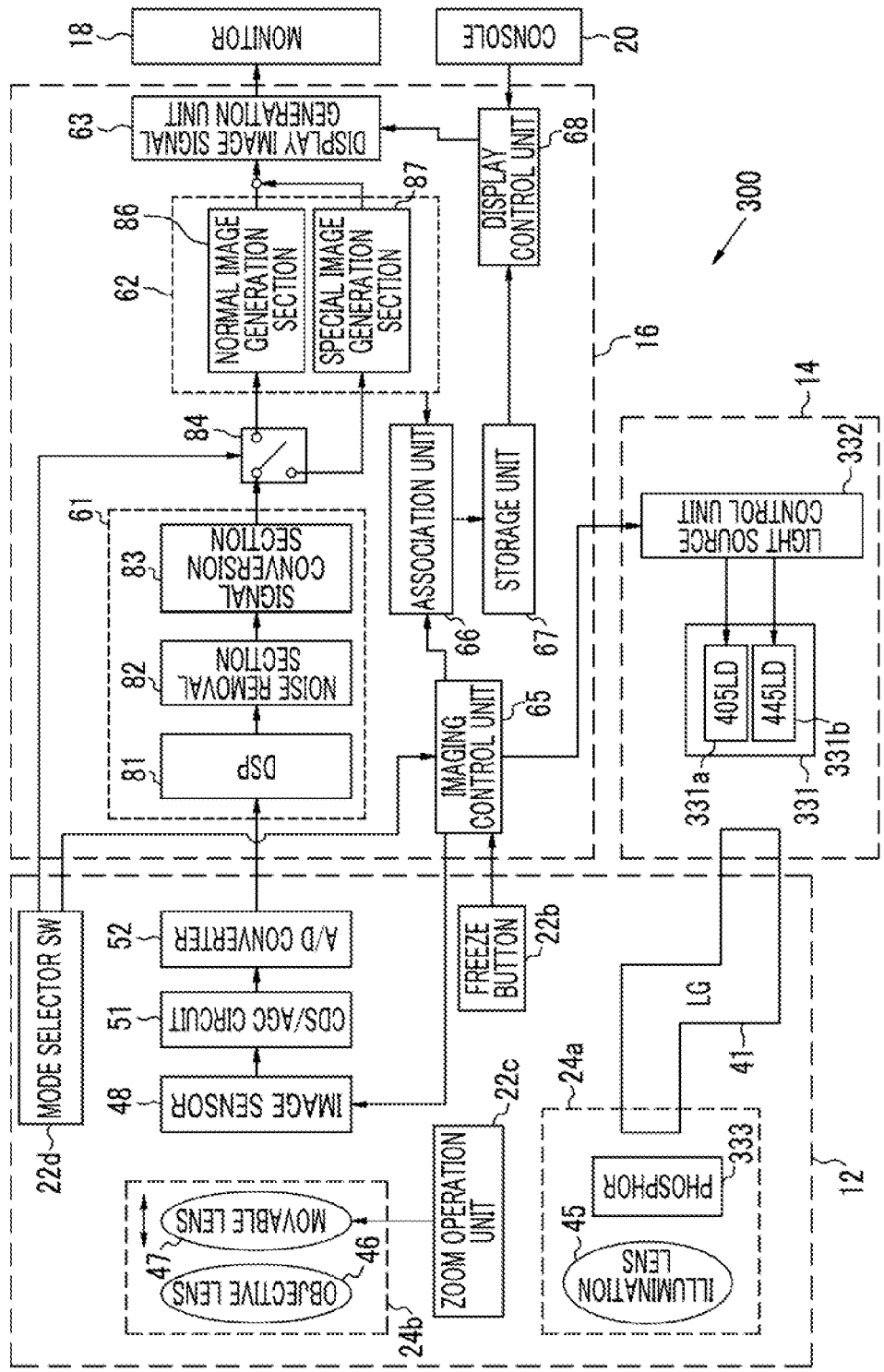
FIG. 18 is a block diagram of an endoscope system that generates illumination light using a laser diode and a phosphor.

In the first and second embodiments described above, the light source device 14 generates illumination light using the LED light source unit 31. However, it is also possible to generate illumination light using a laser diode (LD) and a phosphor, which absorbs some of laser light emitted from the LD and emits fluorescence, instead of the LED light source unit 31 and the light source control unit 32 for controlling the LED light source unit 31. In addition, for example, as in an endoscope system 300 shown in FIG. 18, a laser diode (LD) unit 331 and a light source control unit 332 that controls the LD unit 331 are provided in the light source device 14. In the illumination optical system 24a, a phosphor 333 is provided at a position where laser light that is emitted from the LD unit 331 and is guided by the light guide 41. Except for these, the endoscope system 300 shown in FIG. 18 is the same as the endoscope system 10 according to the first embodiment.

In the LD unit 331, for example, a 405LD 331a that emits violet laser light having a center wavelength of 405 nm and a 445LD 331b that emits blue laser light having a center wavelength of 445 nm are provided. In addition, the phosphor 333 is a phosphor that absorbs some of violet laser light and blue laser light and emits fluorescence of green to yellow (for example, a YAG-based phosphor or BAM ($BaMgAl_{10}O_{17}$)).

Figure 19:
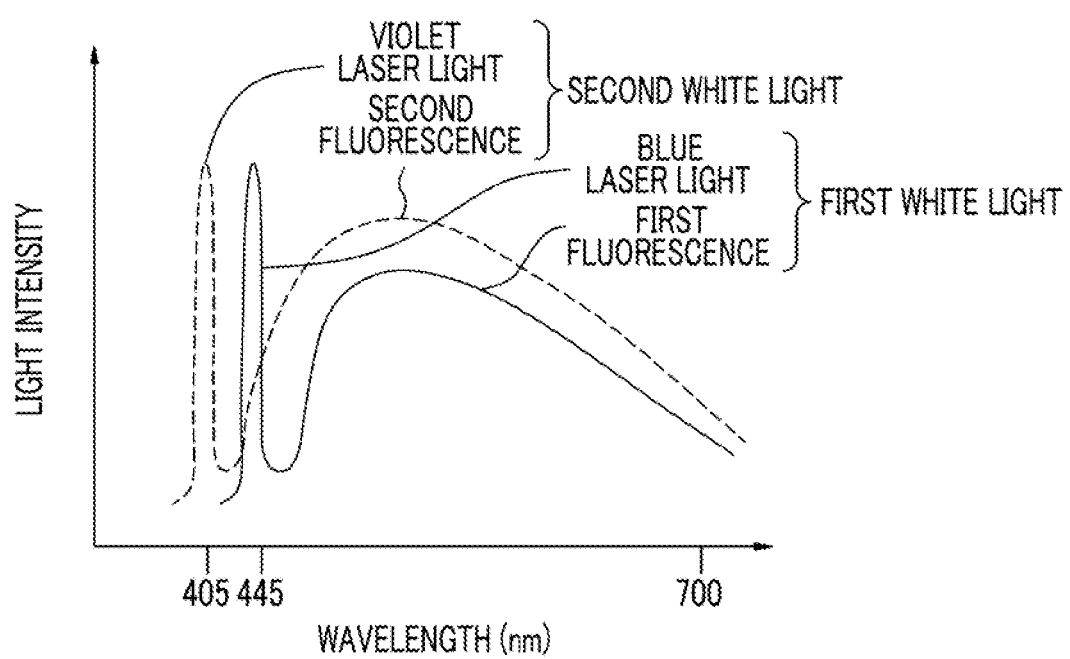
FIG. 19 is a graph showing the spectrum of light by a laser diode and a phosphor.

As shown in FIG. 19, in the normal observation mode, the light source control unit 332 can generate white normal light by turning on the 405LD 331a and the 445LD 331b with a light amount ratio set in advance and combining first white light, which is formed by blue laser light transmitted through the phosphor 333 and first fluorescence emitted from the phosphor 333 that absorbs some of the blue laser light, and second white light, which is formed by violet laser light transmitted through the phosphor 333 and second fluorescence emitted from the phosphor 333 that absorbs some of the violet laser light. Therefore, also in the endoscope system 300 using the LD, it is possible to acquire almost the same image signal as in the first embodiment in the normal observation mode.

In the special observation mode, the light source control unit 332 sets light, which is reflected by the observation target and is then incident on the B pixel of the image sensor 48, to approximate blue light or approximately violet light by adjusting the light amount ratio between the 405LD 331a and the 445LD 331b (or by turning off one of the 405LD 331a and the 445LD 331b). Therefore, also in the endoscope system 300 using the LD, it is possible to realize a special observation mode in which almost the same image signal as in the first embodiment is obtained.

Figure 20:
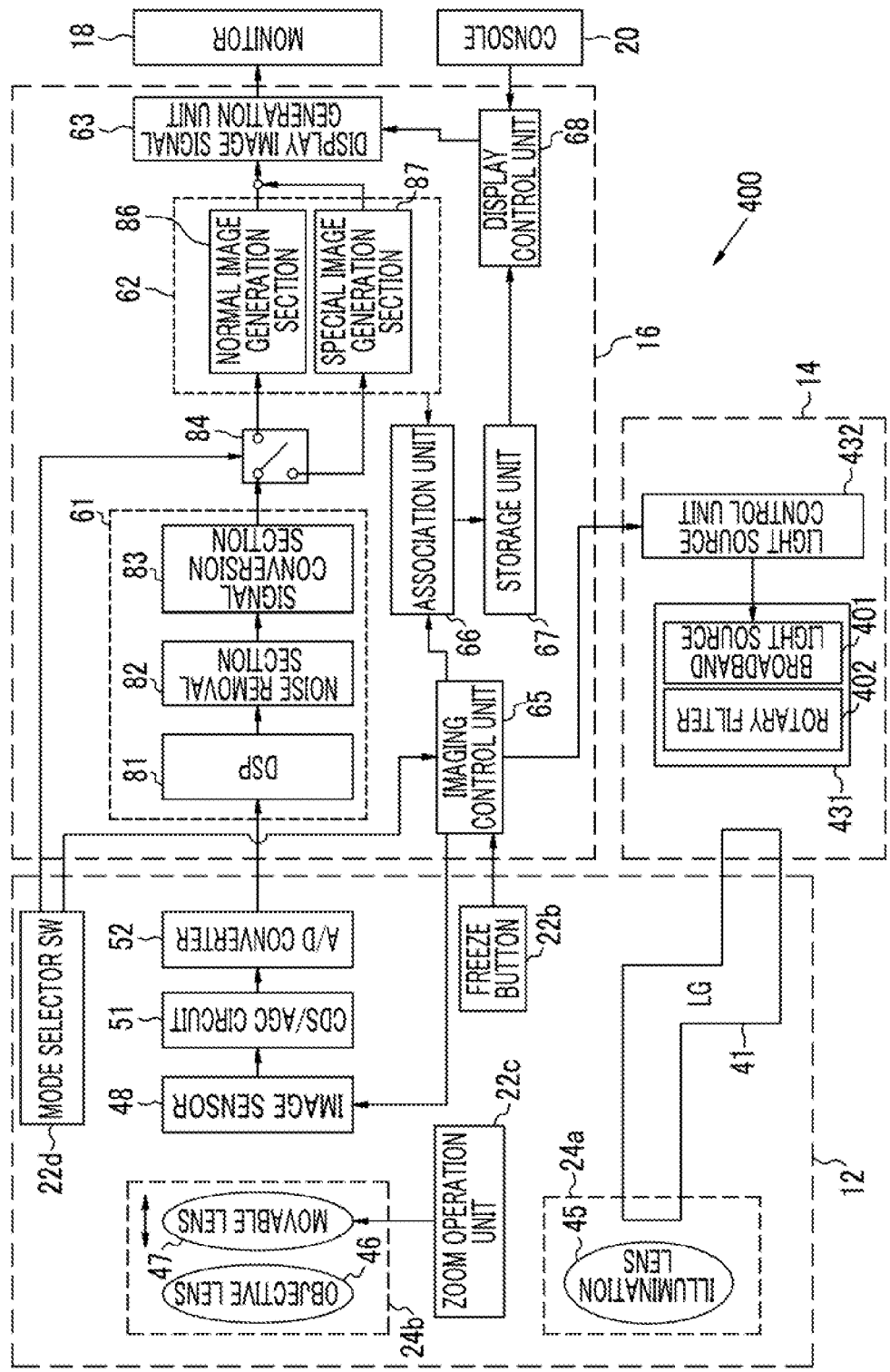
FIG. 20 is a block diagram of an endoscope system that generates illumination light using a broadband light source and a rotary filter.

In addition, as in an endoscope system 400 shown in FIG. 20, a light source unit 431 including a broadband light source 401 and a rotary filter 402 and a light source control unit 432 that controls the light source unit 431 may be used as the light source device 14, instead of the LED light source unit 31 and the light source control unit 32. The broadband light source 401 is, for example, a halogen lamp or a white LED, and generates white broadband light. The amount of broadband light is controlled by the light source control unit 432. The rotary filter 402 is rotatably disposed in the optical path of the broadband light emitted from the broadband light source 401, and limits the wavelength band of the broadband light so that the broadband light in the limited wavelength band is incident on the light guide 41.

Figure 21:
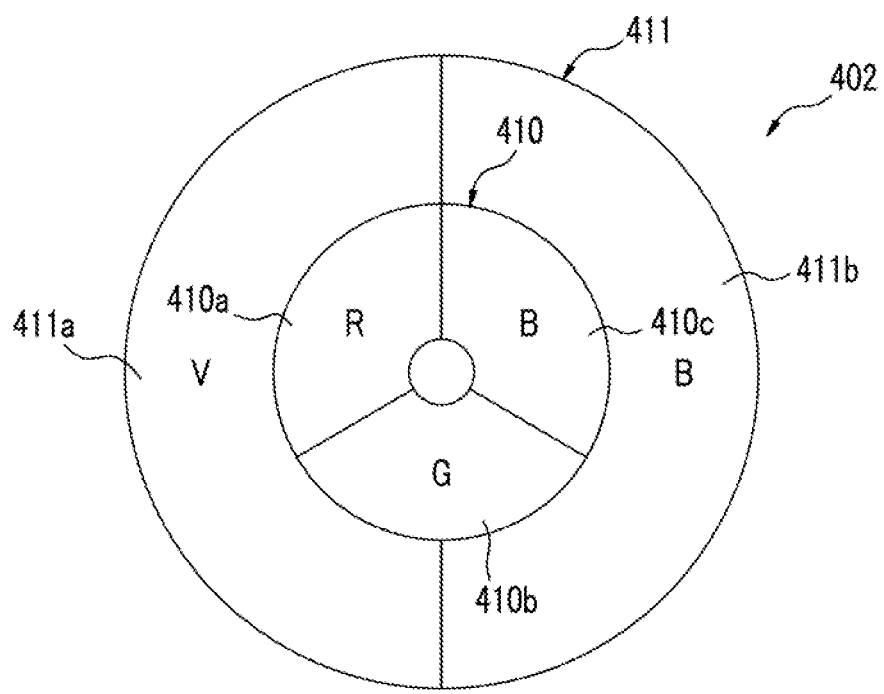
FIG. 21 is an explanatory diagram of a rotary filter.

As shown in FIG. 21, the rotary filter 402 has a normal observation mode filter 410 and a special observation mode filter 411. The normal observation mode filter 410 includes a red filter (R) 410a that transmits red light, a green filter (G) 410b that transmits green light, and a blue filter (B) 410c that transmits blue light. The special observation mode filter 411 includes a violet filter (V) 411a that transmits violet light and a blue filter (B) 411b that transmits blue light. The normal observation mode filter 410 or the special observation mode filter 411 is disposed in the optical path of broadband light according to the set mode by the light source control unit 432, and the rotary filter 402 is rotated in synchronization with the imaging frame of the image sensor 48.

Accordingly, in the endoscope system 400 that generates illumination light using the broadband light source 401 and the rotary filter 402, image signals of respective colors that are simultaneously acquired in the endoscope system 10 according to the first embodiment can be sequentially acquired. In the endoscope system 400 that generates illumination light using the broadband light source 401 and the rotary filter 402, a monochrome image sensor may be used instead of the image sensor 48 that is a color imaging element.

In the first and second embodiments described above, each of the endoscope systems 10 and 200 has a normal observation mode and a special observation mode for emphasis observation of the travel pattern or the like of the blood vessel. However, instead of the special observation mode for emphasis observation of the travel pattern or the like of the blood vessel or in addition to the special observation mode, each of the endoscope systems 10 and 200 may have a second special observation mode to calculate the oxygen saturation of the observation target.

In the first and second embodiments described above, the association unit 66 temporarily stores a plurality of observation images generated by the image generation unit 62, and stores one of the observation images in the storage unit 67, as the first still image, in response to the operation of the freeze button 22b or the zoom operation unit 22c. However, instead of the observation images generated by the image generation unit 62, image signals for generating the observation images may be temporarily stored in the association unit 66. In this case, the association unit 66 acquires image signals of respective colors from the signal conversion section 83 and temporarily stores the image signals. In addition, instead of storing the first still image and the associated video or the second still image in the storage unit 67 so as to be associated with each other in response to the operation of the freeze button 22b or the zoom operation unit 22c as in the first and second embodiments described above, the first still image and the image signal for generating the associated video or the second still image are stored in the storage unit 67 so as to be associated with each other. When performing re-diagnosis or the like, the display control unit 68 reads the image signal stored in the storage unit 67, generates the first still image or the associated video or the second still image using the image generation unit 62, and displays these on the monitor 18.

In this manner, it is possible to reduce the amount of data stored in the association unit 66 or the storage unit 67 and to obtain the first still image and the associated video or the second still image. For example, when storing the first and second still images in the storage unit 67 so as to be associated with each other in the special observation mode, it is necessary to store the data of a total of six channels of data of three channels of BGR of the first still image and data of three channels of BGR of the second still image in order to store the first and second still images in the storage unit 67. On the other hand, the first and second still images in the special observation mode are generated from the data of two channels of a B image signal obtained under violet light and a G image signal obtained under green light. Therefore, if image signals are stored, it is possible to reproduce the first and second still images in the special observation mode simply by storing the data of a total of four channels.

Storing the image signals for generating an image or a video in the storage unit 67 as described above instead of storing images (first and second still images) or a video (associated video) in the storage unit 67 is particularly effective in an endoscope system having an observation mode in which the observation target is observed substantially at the same time by a plurality of observation modes (hereinafter, referred to as a multi-observation mode). Hereinafter, the configuration and operation of an endoscope system having a multi-observation mode will be described.

Figure 22:
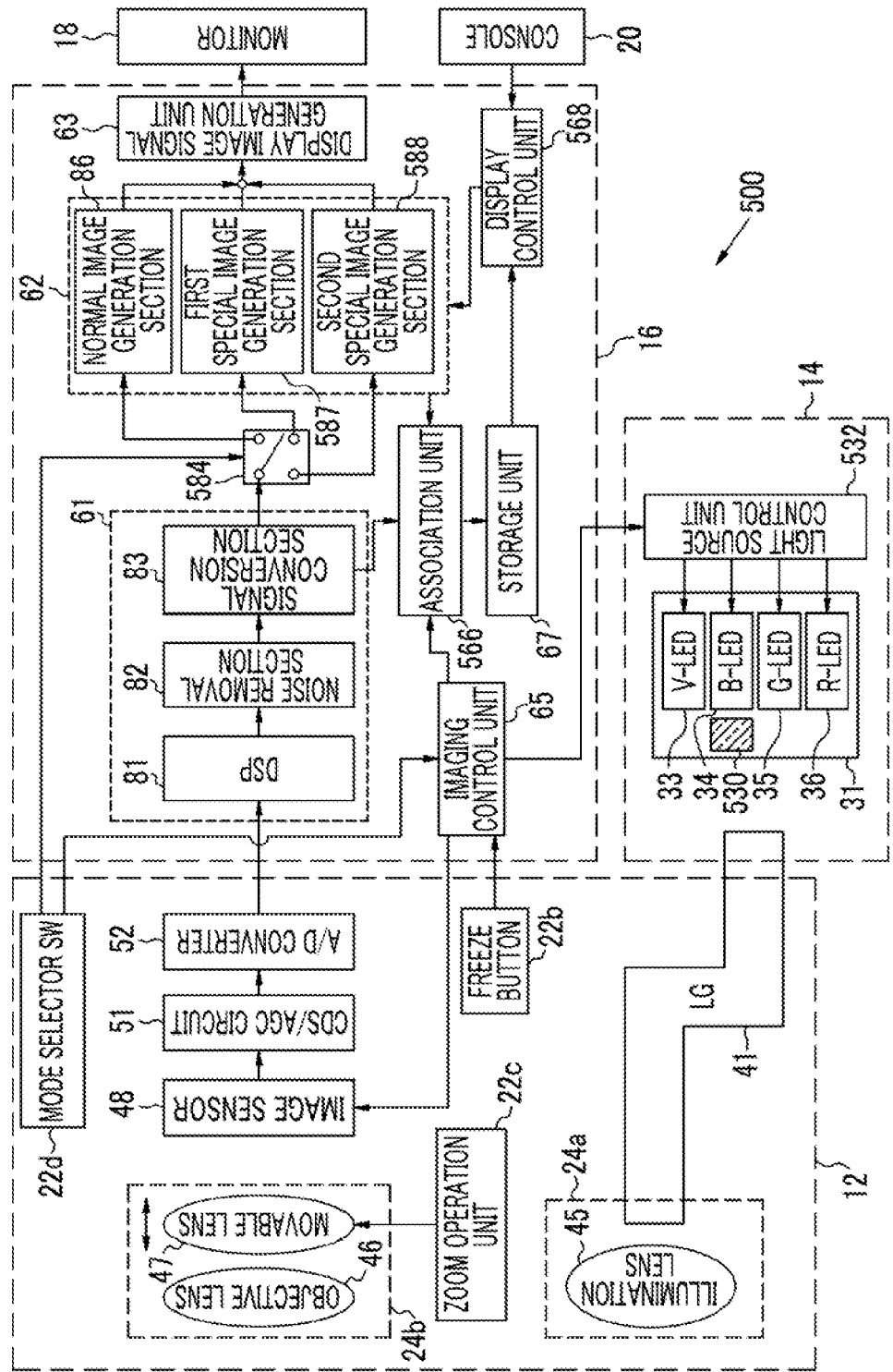
FIG. 22 is a block diagram of an endoscope system having a multi-observation mode.

An endoscope system 500 shown in FIG. 22 includes an optical filter 530 in the LED light source unit 31, and includes a light source control unit 532 instead of the light source control unit 32 of the endoscope system 10 according to the first embodiment. The processor device 16 includes an association unit 566, a display control unit 568, an image processing switching unit 584, and a first special image generation section 587 instead of the association unit 66, the display control unit 68, the image processing switching unit 84, and the special image processing section 87. The image generation unit 62 further includes a second special image generation section 588. Other configurations are the same as the endoscope system 10 according to the first embodiment.

The endoscope system 500 has a normal observation mode, a first special observation mode, a second special observation mode, and a multi-observation mode as observation modes. The normal observation mode is a mode in which the observation target is observed using the white light, and the first special observation mode is a mode in which the travel pattern or the like of the blood vessel of the observation target is emphasized and observed using the violet light and the green light as illumination light. That is, the normal observation mode is the same as the normal observation mode in the first embodiment, and the first special observation mode is the same as the special observation mode in the first embodiment.

In the second special observation mode, the observation target is imaged using the blue light in a wavelength band where the absorption coefficient changes according to the oxygen saturation, and the oxygen saturation of the observation target is calculated based on the obtained image signal. Then, an oxygen saturation image showing the oxygen saturation of the observation target is displayed on the monitor 18 as an observation image. In the multi-observation mode, a normal observation image obtained in the normal observation mode, a special observation image (special observation image in which blood vessels or the like are emphasized) obtained in the first special observation mode, and an oxygen saturation image in the second special observation mode are displayed side by side in almost real time on the monitor 18.

In order to realize these observation modes (especially the second special observation mode), the endoscope system 500 includes the LEDs 33 to 36 of respective colors of the first embodiment in the LED light source unit 31, and further includes the optical filter 530, which limits the wavelength band of blue light emitted from the B-LED 34 to a wavelength band where the absorption coefficient changes according to the oxygen saturation, on the optical path of the B-LED 34. Although the optical filter 530 can be freely inserted and removed at the insertion position on the optical path of the B-LED 34 and the retracted position that is retracted from the optical path of the B-LED 34, the optical filter 530 is disposed at the insertion position regardless of the observation mode and the like in the following explanation.

The light source control unit 532 controls ON/OFF of each of the LEDs 33 to 36, the amount of emitted light, or the like according to the set observation mode. Specifically, when the observation mode is set to the normal observation mode, the light source control unit 532 turns on all of the LEDs 33 to 36 of respective colors so that the LEDs 33 to 36 emit light with the amount of light set in advance. In this case, the wavelength band of the blue light emitted from the B-LED 34 is limited by the optical filter 530, but almost the same white light as in the first embodiment is emitted to the observation target as illumination light. When the observation mode is set to the first special observation mode, the light source control unit 532 turns on the V-LED 33 and the G-LED 35 and turns off the B-LED 34 and the R-LED 36. Therefore, in the first special observation mode, the blue light whose wavelength band is limited by the optical filter 530 and the green light are emitted to the observation target as illumination light.

In addition, when the observation mode is set to the second special observation mode for acquiring an oxygen saturation image, the light source control unit 532 emits two types of illumination light to the observation target alternately in synchronization with the imaging frame of the image sensor 48. More specifically, the light source control unit 532 turns on the B-LED 34 and turns off the V-LED 33, the G-LED 35, and the R-LED 36 corresponding to the first frame. Then, the light source control unit 532 turns on all of the LEDs 33 to 36 of respective colors corresponding to the second frame subsequent to the first frame. Accordingly, the blue light whose wavelength band is limited by the optical filter 530 is emitted to the observation target as illumination light in the first frame, and the white light is emitted to the observation target as illumination light in the second frame.

Figure 23:
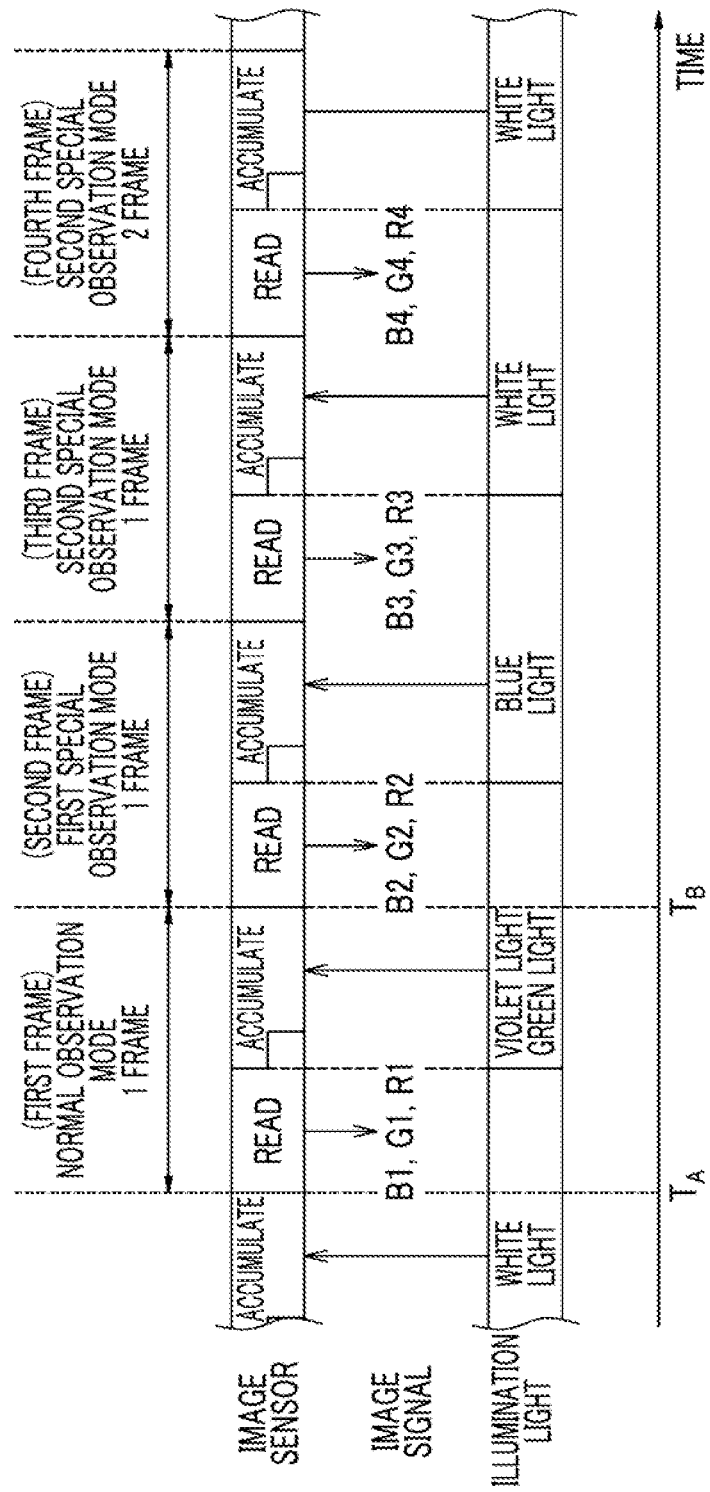
FIG. 23 is an explanatory diagram showing the imaging control in the multi-observation mode.

In addition, when the observation mode is set to the multi-observation mode, the light source control unit 532 performs control in the above-described observation modes sequentially in synchronization with the imaging frame of the image sensor 48 as shown in FIG. 23. That is, all of the LEDs 33 to 36 of respective colors are turned on corresponding to the first frame (corresponding to the normal observation mode), and the V-LED 34 and the G-LED 35 are turned on corresponding to the second frame (corresponding to the first special observation mode). Then, the B-LED 34 is turned on corresponding to the third frame (corresponding to the first frame in the second special observation mode), and all of the LEDs 33 to 36 of respective colors are turned on corresponding to the fourth frame (corresponding to the second frame in the second special observation mode).

Therefore, the image sensor 48 outputs an image signal obtained by imaging the observation target with the reflected light of white light in the first frame, and outputs an image signal obtained by imaging the observation target with the reflected light of violet light and green light in the second frame. Then, the image sensor 48 outputs an image signal obtained by imaging the observation target with the reflected light of blue light in the third frame, and outputs an image signal obtained by imaging the observation target with the reflected light of white light in the fourth frame. In the following explanation, in order to distinguish image signals of respective colors for each frame, image signals of respective colors output from the image sensor 48 in the first frame are referred to as a B1 image signal, a G1 image signal, and an R1 image signal, and image signals of respective colors output from the image sensor 48 in the second frame are referred to as a B2 image signal, a G2 image signal, and an R2 image signal. Similarly, image signals of respective colors output from the image sensor 48 in the third frame are referred to as a B3 image signal, a G3 image signal, and an R3 image signal, and image signals of respective colors output from the image sensor 48 in the fourth frame are referred to as a B4 image signal, a G4 image signal, and an R4 image signal.

FIG. 23 shows an operation when the image sensor 48 is a CCD image sensor, and one frame is a period of the length from the end (time $T_A$) of a charge accumulation period (also referred to as an exposure period) to the end (time $T_B$) of the next charge accumulation period, for example. The generation timing of various kinds of illumination light controlled by the light source control unit 532 synchronizes with an accumulation period when the image sensor 48 accumulates a signal charge by photoelectric conversion. In addition, one frame is divided into a reading period for reading the image signal and a charge accumulation period. However, when the sensor 48 is a CCD image sensor, approximately the entire one frame can be set as a charge accumulation period, and signal charges accumulated in the previous frame can be read during the accumulation of signal charges. In the case of using a CMOS image sensor as the image sensor 48, control for synchronization with the light source control unit 532 that is different from that when the image sensor 48 is a CCD image sensor is required according to the operating characteristics of the CMOS image sensor. However, since the image signal acquired in each frame in each observation mode is the same as that when the image sensor 48 is a CCD image sensor, explanation thereof will be omitted.

The association unit 566 of the endoscope system 500 acquires image signals of respective colors of BGR for generating an observation image from the signal conversion section 83 and temporarily stores the image signals. Then, when a storage instruction is input from the imaging control unit 65 by operating the freeze button 22b, an image signal for generating the first observation image and an image signal for generating the associated video in the first embodiment are associated with each other and are stored in the storage unit 67. That is, the association unit 566 of the endoscope system 500 stores image signals for generating an observation image instead of the observation image. In addition, when a storage instruction is received from the imaging control unit 65 as in the first embodiment, an image signal for generating the first still image and an image signal for generating a video associated with the first still image are associated with each other and are stored in the storage unit 67.

The association unit 566 stores only the minimum image signals required for generating the first still image and the associated video in the storage unit 67, as image signals for generating the first still image and the associated video, instead of storing all image signals obtained by imaging in the storage unit 67. For example, in the multi-observation mode, only image signals of nine channels of a B1 image signal, a G1 image signal, an R1 image signal, a B2 image signal, a G2 image signal, a B3 image signal, a B4 image signal, a G4 image signal, and an R4 image signal among the image signals of twelve channels obtained from the first frame to the fourth frame are stored in the storage unit 67 in response to the storage instruction. This is the same for the case of the first special observation mode or the second special observation mode.

When performing re-diagnosis and the like, the display control unit 568 reads the image signals stored in the storage unit 67 in response to the operation of the console 20, generates the first still image and the associated video using the image generation unit 62, and displays these on the monitor 18. The method of displaying images on the monitor 18 is the same as that in the first embodiment.

The image processing switching unit 584 inputs image signals of respective colors, which are output from the signal conversion section 83, to a processing unit corresponding to the set observation mode since the normal image generation section 86, the first special image generation section 587, and the second special image generation section 588 are provided in the image generation unit 62. That is, the image processing switching unit 584 inputs an image signal to the normal image generation section 86 in the observation mode, inputs an image signal to the first special image generation section 587 in the first special observation mode, and inputs an image signal to the second special image generation section 588 in the second special observation mode. Then, in the multi-observation mode, the image processing switching unit 584 inputs an image signal obtained in the first frame to the normal image generation section 86, inputs an image signal obtained in the second frame to the first special image generation section 587, and inputs image signals obtained in the third and fourth frames to the second special image generation section 588.

The normal image generation section 86 generates a normal observation image based on the input image signal as in the first embodiment. In addition, the first special image generation section 587 generates a first special observation image based on the input image signal. The method of generating the first special observation image is the same as the method of generating the special observation image in the first embodiment. Therefore, the first special observation image is an observation image in which the travel pattern or the like of the blood vessel of the observation target is emphasized.

The second special image generation section 588 calculates the oxygen saturation of the observation target based on the input image signal first. In the second special observation mode, the oxygen saturation is calculated for each pixel based on the ratio between the B image signal obtained in the first frame and the G image signal obtained in the second frame. More specifically, the second special image generation section 588 has a table in which the ratio between image signals set in advance by an experiment or the like is matched with the oxygen saturation, and calculates the oxygen saturation from the ratio between image signals with reference to the table. Similarly, in the multi-observation mode, the oxygen saturation is calculated for each pixel based on the ratio between the B3 image signal obtained in the third frame and the G4 image signal obtained in the fourth frame.

After the oxygen saturation is calculated as described above, the second special image generation section 588 generates an oxygen saturation image (second special image). In the second special observation mode, for example, the second special image generation section 588 multiples image signals (or one of these image signals) of respective colors of BGR obtained in the second frame by the gain corresponding to the oxygen saturation for each pixel, and generates an observation image using each image signal multiplied by the gain. The observation image generated in this manner is an oxygen saturation image. In the oxygen saturation image, the observation target is pseudo-colored by being colored according to the oxygen saturation. This is the same for the case of the multi-observation mode. An oxygen saturation image is generated by multiplying the B4 image signal, the G4 image signal, and the R4 image signal, which are obtained in the fourth frame, by the gain corresponding to the oxygen saturation and generating an observation image using each image signal multiplied by the gain.

In the normal observation mode, the endoscope system 500 configured as described above operates in the same manner as in the normal observation mode of the endoscope system 10 according to the first embodiment. Also in the first special observation mode and the second special observation mode, the endoscope system 500 configured as described above operates in the same manner as in the special observation mode of the endoscope system 10 according to the first embodiment.

However, in the endoscope system 500, when the freeze button 22b is pressed, only the minimum image signals for generating the first still image and the associated video are stored in the storage unit 67 instead of storing the first still image and the associated video in the storage unit 67. Therefore, in the first special observation mode and the second special observation mode, the amount of data stored in the storage unit 67 is reduced more than the endoscope system 10 according to the first embodiment.

For example, in the endoscope system 10 according to the first embodiment, assuming that the number of frames of the associated video is "N", data of three channels of BGR of the first still image and data of three channels of BGR of the associated video need to be stored by N frames. Accordingly, data of "3×(N+1)" channels are stored by the pressing of the freeze button 22b. In contrast, in the endoscope system 500, in the first special observation mode, data of two channels of BG for generating the first still image and data of two channels of BG for generating the first special image of N frames of the associated video are stored in the storage unit. Therefore, in the endoscope system 500, in the first special observation mode, data of "2×(N+1)" channels is stored by the pressing of the freeze button 22b. As a result, the amount of data that is stored is reduced more than that in the case where the first still image and the associated video are stored. This is the same for the second special observation mode. Among the data of six channels obtained by imaging, only the data of four channels required for generating the first still image and the associated video is stored in the storage unit 67. Therefore, the amount of data stored in the storage unit 67 is reduced.

In the endoscope system 500, in the multi-observation mode, a normal observation video formed by normal observation images, a video formed by first special observation images (first special observation video), and a video formed by second special observation images (second special observation video) are displayed almost simultaneously in real time on the monitor 18. Then, when the freeze button 22b is pressed, minimum image signals for generating three kinds of first still images of a normal observation image, a first special observation image, and a second special observation image and minimum image signals for generating three kinds of associated videos of a normal observation video, a first special observation video, and a second special observation video associated with the normal observation image, the first special observation image, and the second special observation image, respectively, are stored in the storage unit 67. Therefore, the amount of data stored in the storage unit 67 can be greatly reduced compared with a case where three kinds of first still images and three kinds of associated videos corresponding thereto are stored in the storage unit 67 as they are.

In the endoscope system 500 described above, corresponding to the endoscope system 10 according to the first embodiment, the first still image and the associated video are stored in the storage unit 67 in response to the operation of the freeze button 22b. However, also in the endoscope system 200 according to the second embodiment in which the first still image and the second still image (or the associated video) are stored in the storage unit 67 according to the operation of the zoom operation unit 22c, image signals may be stored in the storage unit 67 as in the endoscope system 500 described above.

Figure 24:
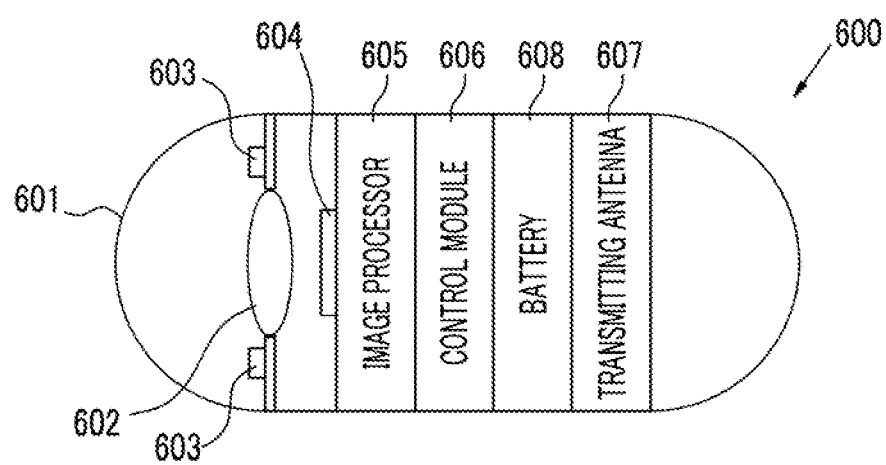
FIG. 24 is an explanatory diagram of a capsule type endoscope system.

In addition, the invention can also be applied to a capsule type endoscope system that is used in a state of being swallowed by the subject. As shown in FIG. 24, a capsule type endoscope system 600 includes an imaging optical system 602, an LED light source unit 603, an image sensor 604, an image processor 605, a control module 606, a transmitting and receiving antenna 607 for transmitting and receiving a control signal or a captured image to and from an external device, and a battery 608 for supplying electric power to these components, and all of these are provided in a capsule housing 601. The imaging optical system 602, the LED light source unit 603, and the image sensor 604 are configured similar to the imaging optical system 24b, the LED light source unit 31, and the image sensor 48 of the endoscope system 10. The image processor 605 has functions of the CDS/AGC circuit 51, the A/D converter 52, the image signal acquisition processing unit 61, and the image generation unit 62 of the endoscope system 10. The control module 606 has functions of the imaging control unit 65, the association unit 66, the storage unit 67, the display control unit 68, and the light source control unit 32 of the endoscope system 10, and operates similar to the endoscope systems 10 and 200 according to the first and second embodiments or the endoscope systems of other modifications based on the control signal, such as a first still image acquisition instruction input through the transmitting and receiving antenna 607.

What is claimed is:

1. An endoscope system, comprising:
an acquisition unit that acquires a first still image and a video or a second still image before and after acquisition of the first still image based on an image signal obtained by imaging an observation target using an image sensor;
an association unit that associates the first still image with the video or associates the first still image with the second still image; and
a storage unit that stores the first still image and the video associated with each other or stores the first still image and the second still image associated with each other;
an imaging optical system capable of changing an imaging magnification of the observation target;
an imaging magnification change operation unit for inputting an imaging magnification change instruction to change the imaging magnification to the imaging optical system; and
a control unit that performs control to acquire the first still image and start acquisition of the video when the imaging magnification change instruction is detected, and to end the acquisition of the video when an operation end of the imaging magnification change operation unit is detected.

2. The endoscope system according to claim 1, further comprising:
a first still image acquisition operation unit for inputting a first still image acquisition instruction to acquire the first still image; and
a control unit that performs control to acquire the first still image based on the first still image acquisition instruction and to automatically acquire the video.

3. The endoscope system according to claim 2,
wherein a first mode and a second mode different from the first mode are prepared as modes for acquiring the first still image and the video or the second still image, and
the control unit performs control to acquire the first still image by one of the first and second modes based on the first still image acquisition instruction and then acquire the video by switching the one mode to the other mode.

4. The endoscope system according to claim 1, further comprising:
an imaging optical system capable of changing an imaging magnification of the observation target;
an imaging magnification change operation unit for inputting an imaging magnification change instruction to change the imaging magnification to the imaging optical system; and
a control unit that performs control to acquire the first still image based on the imaging magnification change instruction and to acquire the second still image after acquisition of the first still image.

5. The endoscope system according to claim 4,
wherein a first mode and a second mode different from the first mode are prepared as modes for acquiring the first still image and the video or the second still image, and
the control unit performs control to acquire the first still image in one of the first and second modes and then acquire the second still image by switching the one mode to the other mode.

6. The endoscope system according to claim 4, further comprising:
a focus detection unit that detects a focus of an image to be acquired,
wherein the control unit performs control to acquire the first still image when an operation of increasing the imaging magnification using the imaging magnification change operation unit is detected and to acquire the second still image when the focus detection unit detects that the image is in focus after acquisition of the first still image.

7. The endoscope system according to claim 5, further comprising:
a focus detection unit that detects a focus of an image to be acquired, wherein the control unit performs control to acquire the first still image when an operation of increasing the imaging magnification using the imaging magnification change operation unit is detected and to acquire the second still image when the focus detection unit detects that the image is in focus after acquisition of the first still image.

8. The endoscope system according to claim 4, wherein the control unit performs control to acquire the first still image when an operation of reducing the imaging magnification using the imaging magnification change operation unit is detected and to acquire the second still image when an operation end of the imaging magnification change operation unit is detected after acquisition of the first still image.

9. The endoscope system according to claim 5, wherein the control unit performs control to acquire the first still image when an operation of reducing the imaging magnification using the imaging magnification change operation unit is detected and to acquire the second still image when an operation end of the imaging magnification change operation unit is detected after acquisition of the first still image.

10. The endoscope system according to claim 6, wherein the control unit performs control to acquire the first still image when an operation of reducing the imaging magnification using the imaging magnification change operation unit is detected and to acquire the second still image when an operation end of the imaging magnification change operation unit is detected after acquisition of the first still image.

11. The endoscope system according to claim 1, further comprising:
an imaging optical system capable of changing an imaging magnification of the observation target;
an imaging magnification change operation unit for inputting an imaging magnification change instruction to change the imaging magnification to the imaging optical system; and
a control unit that performs control to acquire the first still image and start acquisition of the video based on the imaging magnification change instruction, and to end the acquisition of the video when an operation end of the imaging magnification change operation unit is detected.

12. The endoscope system according to claim 11, wherein a first mode and a second mode different from the first mode are prepared as modes for acquiring the first still image and the video or the second still image, and
the control unit performs control to acquire the first still image by one of the first and second modes and then start acquisition of the video by switching the one mode to the other mode.

13. The endoscope system according to claim 1, further comprising:
a display control unit that displays a plurality of the first still images stored in the storage unit side by side on a monitor; and
a selection unit for selecting the plurality of first still images displayed side by side on the monitor,
wherein, when the video associated with the first still images is stored in the storage unit, the display control unit displays the first still image selected by the selection unit on the monitor in an enlarged manner and reproduces the video, which is associated with the selected first still image, on the monitor.

14. The endoscope system according to claim 2, further comprising:
a display control unit that displays a plurality of the first still images stored in the storage unit side by side on a monitor; and
a selection unit for selecting the plurality of first still images displayed side by side on the monitor,
wherein, when the video associated with the first still images is stored in the storage unit, the display control unit displays the first still image selected by the selection unit on the monitor in an enlarged manner and reproduces the video, which is associated with the selected first still image, on the monitor.

15. The endoscope system according to claim 3, further comprising:
a display control unit that displays a plurality of the first still images stored in the storage unit side by side on a monitor; and
a selection unit for selecting the plurality of first still images displayed side by side on the monitor,
wherein, when the video associated with the first still images is stored in the storage unit, the display control unit displays the first still image selected by the selection unit on the monitor in an enlarged manner and reproduces the video, which is associated with the selected first still image, on the monitor.

16. The endoscope system according to claim 1, further comprising:
a display control unit that displays a plurality of the first still images stored in the storage unit side by side on a monitor; and
a selection unit for selecting the plurality of first still images displayed side by side on the monitor,
wherein, when the second still image associated with the first still images is stored in the storage unit, the display control unit displays the first still image selected by the selection unit on the monitor in an enlarged manner and reproduces the second still image, which is associated with the selected first still image, on the monitor.

17. The endoscope system according to claim 2, further comprising:
a display control unit that displays a plurality of the first still images stored in the storage unit side by side on a monitor; and
a selection unit for selecting the plurality of first still images displayed side by side on the monitor,
wherein, when the second still image associated with the first still images is stored in the storage unit, the display control unit displays the first still image selected by the selection unit on the monitor in an enlarged manner and reproduces the second still image, which is associated with the selected first still image, on the monitor.

18. An operation method for the endoscope system according to claim 1, comprising:
an acquisition step in which an acquisition unit acquires a first still image and a video or a second still image before and after acquisition of the first still image based on an image signal obtained by imaging an observation target using an image sensor;
an association step in which an association unit associates the first still image with the video or associates the first still image with the second still image; and
a storage step in which a storage unit stores the first still image and the video associated with each other or stores the first still image and the second still image associated with each other.

19. A processor device for the endoscope system according to claim 1, comprising:
- an acquisition unit that acquires a first still image and a video or a second still image before and after acquisition of the first still image based on an image signal obtained by imaging an observation target using an image sensor;
- an association unit that associates the first still image with the video or associates the first still image with the second still image; and
- a storage unit that stores the first still image and the video associated with each other or stores the first still image and the second still image associated with each other.

20. An operation method for the processor device according to claim 19 for an endoscope system, comprising:
- an acquisition step in which an acquisition unit acquires a first still image and a video or a second still image before and after acquisition of the first still image based on an image signal obtained by imaging an observation target using an image sensor;
- an association step in which an association unit associates the first still image with the video or associates the first still image with the second still image; and
- a storage step in which a storage unit stores the first still image and the video associated with each other or stores the first still image and the second still image associated with each other.

* * * * *